(12) United States Patent
Goletz et al.

(10) Patent No.: US 9,527,899 B2
(45) Date of Patent: Dec. 27, 2016

(54) RECOMBINANT HUMAN FOLLICLE-STIMULATING HORMONE

(75) Inventors: Steffen Goletz, Berlin (DE); Lars Stöckl, Berlin (DE)

(73) Assignee: Glycotope GmbH, Berlin (DE)

( * ) Notice: Subject to any disclaimer, the term of this patent is extended or adjusted under 35 U.S.C. 154(b) by 278 days.

(21) Appl. No.: 13/814,059

(22) PCT Filed: Aug. 4, 2011

(86) PCT No.: PCT/EP2011/063492
§ 371 (c)(1),
(2), (4) Date: Feb. 4, 2013

(87) PCT Pub. No.: WO2012/017058
PCT Pub. Date: Feb. 9, 2012

(65) Prior Publication Data
US 2013/0137636 A1     May 30, 2013

(30) Foreign Application Priority Data
Aug. 4, 2010   (EP) .................. PCT/EP2010/004769

(51) Int. Cl.
*C07K 14/59*   (2006.01)
*A61K 38/00*   (2006.01)

(52) U.S. Cl.
CPC ............... *C07K 14/59* (2013.01); *A61K 38/00* (2013.01)

(58) Field of Classification Search
None
See application file for complete search history.

(56) References Cited

U.S. PATENT DOCUMENTS

2010/0028947 A1*  2/2010  Goletz et al. ............... 435/69.6

FOREIGN PATENT DOCUMENTS

| EP | 2325194 A1 | 5/2011 |
|---|---|---|
| WO | 03/035686 A2 | 5/2003 |
| WO | 2009/127826 A1 | 10/2009 |
| WO | 2011/063943 A1 | 6/2011 |

OTHER PUBLICATIONS

Wide, Upsala Journal of Medical Sciences. 2013; 118: 153-164.*
Bousfield et al., J Glycomics Lipidomics 2014, 4:4; 16 pages total.*
Nakamura et al., Reproductive Medicine and Biology 2003; 2: 63-67.*
Byrne, Barry et al., "Sialic acids: carbohydrate moieties that influence the biological and physical properties of biopharmaceutical proteins and living cells," Drug Discovery Today, vol. 12(7/8):319-326 (2007).
Olijve, Wiebe et al., "Molecular biology and biochemistry of human recombinant follicle stimulating hormone (Puregon)," Molecular Human Reproduction, vol. 2(5):371-382 (1996).
International Search Report for Application No. PCT/EP2011/063492, 4 pages, dated Nov. 15, 2011.
International Preliminary Report on Patentability and Written Opinion for Application No. PCT/EP2011/063492, 7 pages, dated Feb. 5, 2013.
Steelman, Sanford L. et al., "Assay of the Follicle Stimulating Hormone Based on the Augmentation with Human Chronic Gonadotropin," Endocrinology, vol. 53(6):604-616 (1953).
Storring, P.L. et al., "The fourth International Standard for Human Urinary FSH and LH: specificities of LH seminal vesicle weight gain assays in the collaborative study differ between laboratories," Journal of Endocrinology, vol. 171:119-129 (2001).
Hard, K. et al., "Isolation and Structure Determination of the Intact Sialylated N-linked Carbohydrate Chains of Recombinant Human Follitropin Expressed in Chinese Hamster Ovary Cells," European Journal of Biochemistry, vol. 193, pp. 263-271 (1990).
Le Cotonnec, J. et al., "Clinical Pharmacology of Recombinant Human Follicle-stimulating Hormone II. Single Doses and Steady State Pharmacokinetics," Fertility and Sterility, vol. 61(4), pp. 679-686 (1994).
Le Cotonnec, J. et al., "Comparative pharmacokinetics of two urinary human follicle stimulating hormone preparations in healthy female and male volunteers," Human Reproduction, vol. 8(10), pp. 1604-1611 (1993).

* cited by examiner

*Primary Examiner* — Christina Borgeest
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to improved FSH preparations which are capable of stimulating sex steroid release at much lower concentration than the commonly used urinary FSH or recombinant FSH obtained from CHO cells and which act independent of cAMP signaling These improved FSH preparations can be used in infertility treatment.

17 Claims, 10 Drawing Sheets

Figure 10
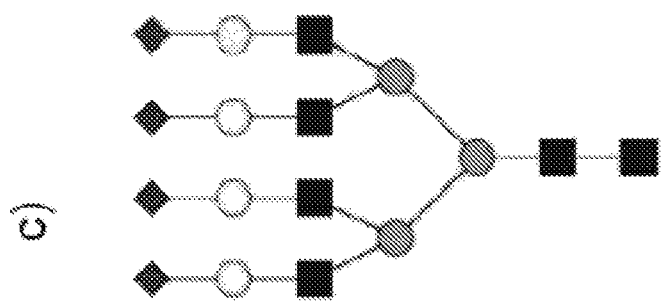
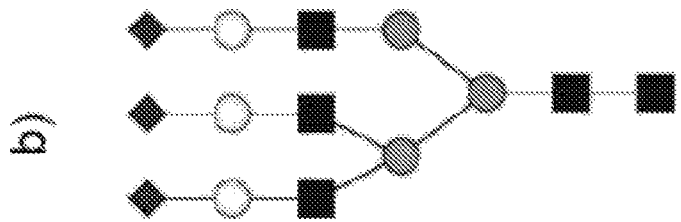
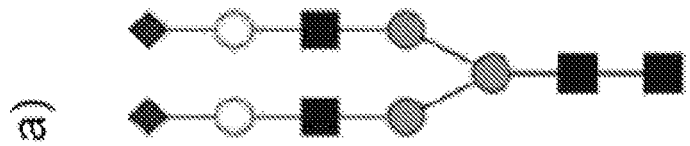

SEQUENCE LISTING

<160> NUMBER OF SEQ ID NOS: 2

<210> SEQ ID NO 1
<211> LENGTH: 92
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

RECOMBINANT HUMAN FOLLICLE-STIMULATING HORMONE

FIELD OF THE INVENTION

The present invention pertains to the field of gonadotropins. In particular, improved recombinant human follicle-stimulating hormone (rhFSH) is provided. This improved rhFSH is useful in the treatment of infertility, in particular in human patients.

BACKGROUND OF THE INVENTION

Gonadotropins are a group of protein hormones which regulate gonadal function in the male and female and thereby play an important role in human fertility. They are secreted by gonadotrope cells of the pituitary gland of vertebrates after stimulation by the gonadotropin-releasing hormone (GnRH). Gonadotropins are heterodimeric glycoproteins including follicle stimulating hormone (FSH), luteinizing hormone (LH) and chorionic gonadotropin (CG). The gonadotropins share identical alpha-subunits but comprise different beta-subunits which ensure receptor binding specificity.

FSH comprises a 92 amino acid alpha-subunit and a 111 amino acid beta-subunit which confers specific binding to the FSH receptor. Both subunits of the natural protein are modified by glycosylation. The alpha-subunit is naturally glycosylated at Asn52 and Asn78 and the beta-subunit at Asn7 and Asn24. Both subunits are produced in the cells as precursor proteins and then processed and secreted. FSH regulates the development, growth, pubertal maturation, and reproductive processes of the body. In particular, it stimulates the maturation of germ cells and thus is involved in spermatogenesis and folliculogenesis.

Folliculogenesis is induced by FSH, for example, by binding of FSH to FSH receptors on the surface of granulosa cells. FSH receptors are G protein-coupled receptors which activate the coupled G protein upon binding of FSH. The G protein in turn activates adenylyl cyclase, resulting in the production of cAMP, a second messenger molecule. The increasing cAMP concentration in the cell aktivates several downstream targets, in particular cAMP dependent protein kinases, which then lead to the synthesis of progesterone and estradiol. The progesterone and estradiol is secreted by the granulosa cells, inducing folliculogenesis. Upon stimulation of the granulosa cells by FSH, they also release inhibin-B which forms a negative feedback loop, inhibiting the production and secretion of FSH in the pituitary gland. Inhibin-B was shown to be a good surrogate marker for the ovarian stimulation by FSH.

FSH is widely used in the treatment of infertility, either alone or in combination with other agents, in particular LH. In the art, generally FSH purified from post-menopausal human urine (urinary FSH) or FSH recombinantly produced by Chinese hamster ovary (CHO) cells has been used for human treatment. However, there is considerable heterogeneity associated with FSH preparations due to different isoforms present. Individual FSH isoforms exhibit identical amino acid sequences but differ in the extent and nature of their glycosylation. Particular isoforms are characterized by heterogeneity of the carbohydrate branch structures and differing amounts of sialic acid (a negatively charged terminal monosaccharide unit) incorporation, both of which influence the specific bioactivity of the isoform. Thus, the glycosylation pattern of the FSH has a significant influence on its biological activity.

However, urinary FSH from different donors and different preparations can significantly vary in its carbohydrate structures, resulting in a high batch-to-batch variation. There are also safety concerns regarding the presence of viruses in the urinary products. Furthermore, FSH obtained from CHO cells exhibits a glycosylation pattern specific for these hamster cells which is not identical to human glycosylation patterns. These differences result in varying biological activities and adverse effects of the obtained FSH and thus, of the pharmaceutical preparations which are to be administered to the patient.

In view of this, it is one object of the present invention to provide improved FSH preparations.

Furthermore, it is an object of the present invention to provide FSH preparations with novel therapeutic or pharmacological characteristics.

Furthermore, it is an object of the present invention to provide FSH preparations which have an improved glycosylation pattern.

SUMMARY OF THE INVENTION

The present inventors have found that improved FSH preparations obtained from human cells which preferably have been selected for an optimized glycosylation are able to induce the secretion of sex steroids such as estradiol and progesterone at lower concentrations than corresponding FSH preparations obtained from human urine or CHO cells. Therefore, the FSH preparations according to the present invention have surprising characteristics which are useful in therapy.

The present invention provides, in a first aspect, a recombinant FSH preparation, wherein the recombinant FSH in the preparation has a glycosylation pattern comprising one or more of the following characteristics:

(i) a relative amount of glycans carrying bisecting N-acetylglucosamine (bisGlcNAc) of at least 20%;
(ii) a relative amount of glycans carrying fucose of at least 30%; and/or
(iii) a relative amount of 2,6-coupled sialic acid of at least 30%; and/or
(iv) it is a diverse glycosylation pattern.

In a second aspect, the present invention provides a recombinant FSH preparation obtainable by production in human cells or a human cell line, preferably in the cell line GT-5s (DSM ACC3078, deposited on Jul. 28, 2010). It was found that FSH produced in a respective cell line results in an improved glycosylation profile as is described above and below.

Also provided is a pharmaceutical composition, comprising the recombinant FSH according to the present invention.

Furthermore, the present invention pertains to the recombinant FSH preparation or the pharmaceutical composition according to the present invention for use in infertility treatment.

Furthermore, the present invention pertains to the recombinant FSH preparation or the pharmaceutical composition according to the present invention for inducing and/or stimulating the secretion of sex steroids also independent of cAMP.

Some experiments have shown that the low concentration effects of the FSH according to the invention are in certain circumstances independent of cAMP signaling in the target cells. Thus, the experiments suggest that the improved FSH preparations according to the present invention may induce the secretion of sex steroids such as progesterone at concentrations without an increase of cAMP secretion. Therefore, it is believed that certain embodiments of the improved FSH preparations according to the present invention are capable of inducing a signal transduction pathway leading to sex steroid secretion which is different from the known signal transduction pathway using cAMP as second messenger described for the commonly used FSH preparations.

Furthermore, the present invention pertains to the recombinant FSH preparation or the pharmaceutical composition according to the present invention for stimulating or co-stimulating germ cell maturation by a biological process which is independent of cAMP signaling.

Furthermore, the present invention pertains to the recombinant FSH preparation or the pharmaceutical composition according to the present invention for inducing and/or stimulating the secretion of sex steroids at FSH concentrations at which no significant cAMP release is induced.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Definitions:

As used herein, the following expressions are generally intended to preferably have the meanings as set forth below, except to the extent that the context in which they are used indicates otherwise.

The expression "comprise", as used herein, besides it's regular meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements.

The term "FSH" refers to follicle-stimulating hormone, a gonadotropin. FSH is a glycoprotein comprised of two subunits, labeled alpha and beta subunits. Preferably, the FSH is human FSH, in particular human FSH composed of an alpha subunit having the amino acid sequence of SEQ ID NO: 1 and an beta subunit having the amino acid sequence of SEQ ID NO: 2. However, one or more, such as 1, 1 or 2, up to 3, up to 5, up to 10 or up to 20, amino acid substitution, addition and/or deletions may be present in one or both subunits. Preferably, the amino acid sequence of the alpha subunit shares an overall homology or identity of at least 80%, more preferably at least 85%, at least 90%, at least 95% or at least 98% with the amino acid sequence according to SEQ ID NO: 1. Furthermore, the amino acid sequence of the beta subunit preferably shares an overall homology or identity of at least 80%, more preferably at least 85%, at least 90%, at least 95% or at least 98% with the amino acid sequence according to SEQ ID NO: 2. The subunits of the FSH are preferably two separate polypeptide chains, however, the term "FSH" as used herein also encompasses embodiments wherein the two subunits are covalently attached to each other, e.g. by cross-linking agents or a linking polypeptide chain, and embodiments, wherein one or both subunits are further divided into several polypeptide chains. Preferably, the FSH according to the invention is capable of binding to and/or activating the FSH receptor, preferably the human FSH receptor. The term "FSH" as used herein in particular refers to all FSH proteins in a preparation. Thus, the term "FSH" in particular refers to the entirety of all FSH proteins in a FSH preparation or composition.

Preferably, both subunits of the FSH protein comprise one or more carbohydrate structures attached to the polypeptide chain. More preferably, the carbohydrate structures are attached to asparagine residues of the subunits. In particularly preferred embodiments, the alpha subunit comprises two carbohydrate structures attached to Asn52 and Asn78 and/or the beta-subunit comprises two carbohydrate structures attached to Asn7 and Asn24. The amino acid residues carrying the carbohydrate structures are designated with respect to the human amino acid sequences of the alpha and beta subunits according to SEQ ID NOs: 1 and 2, respectively. The sugar part of human FSH is preferably composed of fucose, galactose, mannose, galactosamine, glucosamine, and/or sialic acid.

FSH as used according to the present invention preferably is recombinant FSH, more preferably recombinant human FSH. The term "recombinant FSH" refers to FSH which is not naturally produced by a living human or animal body and then obtained from a sample derived therefrom, such as urine, blood or other body liquid, feces or tissue of the human or animal body. Preferably, recombinant FSH is obtained from cells which have been biotechnologically engineered, in particular cells which have been transformed or transfected with a nucleic acid encoding FSH or the alpha or beta subunits of FSH. According to preferred embodiments, recombinant FSH is obtained from human cells comprising an exogenous nucleic and encoding FSH. Respective exogenous nucleic acids can be introduced e.g. by using one or more expression vectors, which can be introduced into the host cell e.g. via transfection. Respective methods for recombinantly producing proteins and FSH are well known in the prior art and thus, need no further description.

The FSH according to the invention preferably is FSH, more preferably human FSH. obtainable by production in a human cell, preferably a human cell line. The human cell line preferably is derived from human blood cells, in particular it is a myeloid cell line, preferably a myeloid leukemia cell line. The cell line preferably is immortalized. In a preferred embodiment, the cell line for the production of the FSH according to the invention is the cell line GT-5s, deposited on Jul. 28, 2010 under the accession number DSM ACC3078 according to the requirements of the Budapest Treaty at the Deutsche Sammlung von Mikroorganismen und Zellkulturen (DSMZ), Inhoffenstraße 7B, 38124 Braunschweig (DE) by the Glycotope GmbH, Robert-Rössle-Str. 10, 13125 Berlin (DE), or a cell line derived therefrom, or a homologous cell line. GT-5s is an immortalized human myeloid leukemia cell line which is capable of providing a specific glycosylation pattern as described herein. According to the present invention, the terms "GT-5s" and "GT-5s cell line" also include cells or cell lines derived from GT-5s. A cell line which is derived from GT-5s can be for example obtained by randomly or specifically selecting a single clone or a group of cells from a GT-5s culture, optionally after treating the GT-5s cells in order to enhance their mutation rate, or by genetically altering a GT-5s cell line. The selected clone or group of cells may further be treated as described above and/or further rounds of selection may be performed.

A cell line which is homologous to GT-5s in particular is an immortalized human myeloid cell line. Preferably, a cell line derived from or homologous to GT-5s is capable of providing FSH having a glycosylation pattern similar to that obtained from GT-5s. Preferably, FSH that is produced by a cell line derived from or homologous to GT-5s has one or more of the glycosylation characteristics as described herein, in particular a relative amount of glycans carrying bisecting N-acetylglucosamine (bisGlcNAc) of at least 20%; and/or a relative amount of glycans carrying fucose of at least 30%; and/or a relative amount of 2,6-coupled sialic acid of at least 30%; and/or a diverse glycosylation pattern. According to one embodiment, the cell line derived from or homologous to GT-5s is capable of expressing FSH having a glycosylation pattern as is described as preferred herein, in particular a glycosylation pattern selected from Table 1. The similar glycosylation pattern of FSH that is produced by the cell line derived from or homologous to GT-5s preferably differs from the glycosylation pattern of FSH obtained from GT-5s by 20% or less, more preferably 15% or less, 10% or less or 5% or less, in particular in one or more, preferably all of the glycosylation properties selected from the group consisting of the relative amount of bisGlcNAc, the relative amount of sialylated glycans, the relative amount of sulfated glycans, the relative amount of 2,6-coupled sialic adds, the relative amount of fucose, the relative amount of tetraantennary glycans, the relative amount of glycan branches carrying galactose, and the Z number. Furthermore, the FSH according to the invention preferably is FSH, more preferably human FSH, having one or more specific glycosylation characteristics as disclosed herein, preferably a glycosylation pattern selected from Table 1. The cell line GT-5s as well as cell lines derived therefrom and cell lines homologous thereto are in particular advantageous since they provide a very stable and homogeneous protein production, in particular with respect to FSH protein. They have a very good batch-to-batch consistency, i.e. the produced proteins and theft glycosylation pattern are similar when obtained from different production runs or when produced at different scales and/or with different culturing procedures. In particular, the diverse glycosylation pattern as described herein is highly reproducible in different production runs using these cell lines for expressing FSH.

The FSH according to the present invention is glycosylated, i.e. it is modified by one or more, preferably four, oligosaccharides attached to the polypeptides chains. These oligosaccharides, also named glycans or carbohydrates, may be linear or branched saccharide chains and preferably are complex-type N-linked oligosaccharide chains. Depending on the number of branches the oligosaccharide is termed mono-, bi-, tri- or tetraantennary (or even pentaantennary). A monoantennary oligosaccharide is unbranched while a bi-, tri- or tetraantennary oligosaccharide has one, two or three branches, respectively. A glycoprotein with a higher antennarity thus has more oligosaccharide endpoints and can carry more functional terminal saccharide units such as, for example, sialic acids. "At least triantennary" as used herein refers to oligosaccharides having an antennarity of at least 3, including triantennary. tetraantennary and pentaantennary oligosaccharides. "At least tetraantennary" as used herein refers to oligosaccharides having an antennarity of at least 4, including tetraantennary and pentaantennary oligosaccharides. With respect to complex-type N-glycans, a bisecting GlcNAc residue preferably is not considered as a branch or antenna and thus, does not add to the antennarity of the FSH.

The glycosylation pattern of FSH as referred to herein in particular refers to the overall glycosylation pattern of all FSH proteins in a FSH preparation according to the present invention. In particular, any glycan structures comprised in the FSH protein and thus, attached to the FSH polypeptide chains in the FSH preparation are considered and reflected in the glycosylation pattern.

The term "sialic acid" in particular refers to any N- or O-substituted derivatives of neuraminic acid. It may refer to both 5-N-acetylneuraminic acid and 5-N-glycolylneuraminic acid, but preferably only refers to 5-N-acetylneuraminic acid. The sialic acid, in particular the 5-N-acetylneuraminic acid preferably is attached to a carbohydrate chain via a 2,3- or 2,6-linkage. Preferably, in the FSH preparations described herein both 2,3- as well as 2,6-coupled sialic acids are present.

The degree of sialylation of FSH is normally expressed as Z-number. The Z-number indicates the relative negative charge of the glycan structures of a glycoprotein. The Z-number is calculated by the formula:

$$Z = A1\% * 1 + A2\% * 2 + A3\% * 3 + A4\% * 4$$

wherein A1% is the percentage of glycans with a charge of −1, A2% is the percentage of glycans with a charge of −2. A3% is the percentage of glycans with a charge of −3, and A4% is the percentage of glycans with a charge of −4. These percentages are calculated with respect to all glycans attached to the FSH, including charged as well as uncharged glycans. The charge of the glycans may be provided by any charged monosaccharide units or substituents comprised in the glycan, in particular by sialic acid residues and/or sulfate groups and/or phosphate groups. Since the charge of the glycans of FSH is generally only determined by their sialic acid residues and FSH generally has four glycan structures, the Z-number is an indication for the amount of sialic acids on the FSH or the acidity of the FSH. However, when the FSH also comprises a significant amount of sulfated glycans, the Z-number is an indication for the combined amounts of sialic acids and sulfate groups.

A "relative amount of glycans" according to the invention refers to a specific percentage or percentage range of the glycans attached to the FSH glycoproteins of a FSH preparation or in a composition comprising FSH, respectively. In particular, the relative amount of glycans refers to a specific percentage or percentage range of all glycans comprised in the FSH proteins and thus, attached to the FSH polypeptide chains in a FSH preparation or in a composition comprising FSH. 100% of the glycans refers to all glycans attached to the FSH glycoproteins of the FSH preparation or in a composition comprising FSH, respectively. For example, a relative amount of glycans carrying bisecting GlcNAc of 60% refers to a FSH preparation wherein 60% of all glycans comprised in the FSH proteins and thus, attached to the FSH polypeptide chains in said FSH preparation comprise a bisecting GlcNAc residue while 40% of all glycans comprised in the FSH proteins and thus, attached to the FSH polypeptide chains in said FSH preparation do not comprise a bisecting GlcNAc residue.

The numbers given herein, in particular the relative amounts of a specific glycosylation property, are preferably to be understood as approximate numbers. In particular, the numbers preferably may be up to 10% higher and/or lower, in particular up to 9%, 8%, 7%, 6%, 5%, 4%, 3%, 2% or 1% higher and/or lower.

A "FSH preparation" may be any composition or substance comprising or consisting of FSH. It may be in solid or fluid form and may comprise further ingredients in addition to FSH. In particular, a FSH preparation may be a solution comprising FSH and a suitable solvent such as water and/or alcohol. or a powder obtained, for example, after lyophilization of a solution containing FSH. Suitable examples of a FSH preparation are composition obtained after expression of FSH in cells, in particular after purification of the FSH, or pharmaceutical compositions comprising FSH. A FSH preparation may contain, in addition to FSH, for example solvents, diluents, excipients, stabilizers, preservatives, salts, adjuvants and/or surfactants. The terms "FSH preparation" is used herein in particular in the meaning of a "composition comprising FSH". These terms are preferably used synonymously herein.

A "relative amount of 2,6-coupled sialic acid" refers to a specific percentage or percentage range of the total amount of sialic acids being 2,6-coupled sialic acids. A relative amount of 2,6-coupled sialic acid of 100% thus means that all sialic acids are 2,6-coupled sialic acids. For example, a relative amount of 2,6-coupled sialic acids of 60% refers to a FSH preparation wherein 60% of all sialic acids comprised in the FSH proteins and thus, attached to the oligosaccharide chains of the FSH proteins in said FSH preparation are attached via a 2,6-linkage while 40% of all sialic acids comprised in the FSH proteins and thus, attached to the oligosaccharide chains of the FSH proteins in said FSH preparation are not attached via a 2,6-linkage, but for example via a 2,3-linkage or a 2,8-linkage.

The term "diverse glycosylation pattern" in particular refers to the glycosylation pattern of the FSH proteins in a preparation or composition which glycosylation pattern comprises multiple different glycan structures. Different glycan structures are oligosaccharide structures which differ in the presence/absence, amount and/or position of at least one monosaccharide unit and/or at least one chemical modification such as e.g. sulfate residues, acetyl residues or the like. A specific "different glycan structure" preferably is only considered in this respect if its relative amount is at least 0.02%, more preferably at least 0.03%, at least 0.05%, at least 0.07%, at least 0.1%, at least 0.15%, at least 0.2%, at least 0.25%, at least 0.3% or at least 0.5% of the total amount of glycan structures in the glycosylation pattern. A diverse glycosylation pattern in particular is a glycosylation pattern which comprises at least 5 different glycan structures. Preferably, the diverse glycosylation pattern comprises at least 7, more preferably at least 10. at least 15, at least 20, at least 25, at least 30, at least 35, at least 40, at least 45, at least 50, at least 55 and most preferably at least 60 different glycan structures. A diverse glycosylation pattern in particular also refers to a glycosylation pattern of FSH in a preparation or composition which glycosylation pattern comprises more different glycan structures than FSH obtained from CHO cells in a respective preparation or composition. In particular, the glycosylation pattern comprises at least 10%, preferably at least 20%, at least 30%, at least 40%, at least 50%. at least 60%, at least 70%, at least 80%, at least 90%, and most preferably at least 100% more different glycan structures than FSH obtained from CHO cells.

The term "nucleic acid" includes single-stranded and double-stranded nucleic acids and ribonucleic acids as well as deoxyribonucleic acids. It may comprise naturally occurring as well as synthetic nucleotides and can be naturally or synthetically modified, for example by methylation, 5'- and/or 3'-capping.

The term "vector" is used herein in its most general meaning and comprises any intermediary vehicle for a nucleic acid which enables said nucleic acid, for example, to be introduced into prokaryotic and/or eukaryotic host cells and, where appropriate, to be integrated into a genome of the host cell. Vectors of this kind are preferably replicated and/or expressed in the host cells. A vector preferably comprises one or more selection markers for selecting host cells comprising the vector. Suitable selection markers are resistance genes which provide the host cell with a resistance IS e.g. against a specific antibiotic. Further suitable selection markers are, for example, genes for enzymes such as DHFR or GS. Vectors enabling the expression of recombinant proteins including FSH as well as suitable expression cassettes and expression elements which enable the expression of a recombinant protein with high yield in a host cell are well known in the prior art and are also commercially available, and thus, need no detailed description here.

The terms "cell" and "cells" and "cell line" used interchangeably, preferably refer to one or more mammalian cells, in particular human cells. The term includes progeny of a cell or cell population. Those skilled in the art will recognize that "cells" include progeny of a single cell, and the progeny can not necessarily be completely identical (in morphology or of total DNA complement) to the original parent cell due to natural, accidental, or deliberate mutation and/or change. "Cell" preferably refers to isolated cells and/or cultivated cells which are not incorporated in a living human or animal body.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being. In case of a human patient, the FSH preferably is human FSH. The patient may be male or female, and preferably is female.

The term "pharmaceutical composition" particularly refers to a composition suitable for administering to a human or animal, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

The international units (IU) for FSH refer to the fourth International Standard for Human Urinary FSH and LH (Stoning, P. L. & Gaines Das, R. E. (2001) Journal of Endocrinology 171, 119-129) and are determined according to the augmented ovarian weight gain method (Steelman, S. L. & Pohley, F. M. (1953) Endocrinology 53, 604-616).

The term "infertility treatment" according to the invention means the treatment of a dysfunction or disease related to the reproduction or fertility of a human or animal subject. In particular, infertility treatment includes assisted reproductive technologies, ovulation induction, in-vitro fertilization, intrauterine insemination, as well as the enablement or improvement of germ cell maturation such as folliculogenesis and spermatogenesis.

According to the invention, the term "wherein no significant amounts of cAMP are released" or similar expressions, respectively, in particular refer to the release of cAMP by cells or tissue in an amount which is less than 25%, preferably less than 20%, more preferably less than 15%, less than 10%, less than 7.5%, less than 5% or less than 2.5% of the amount of cAMP release obtained by cells or tissue after stimulation with FSH in a concentration which results in the maximum release of cAMP. These cells or tissue are susceptible or responsive to stimulation by FSH, such as granulosa cells or Sertoli cells. A cAMP release which is independent of FSH, i.e. a cAMP release which also occurs in the absence of FSH, should not be considered in this respect. Preferably, a "release of a significant amount of cAMP" or a "significant release of cAMP" is any release of cAMP above the cAMP release in the absence of FSH, in particular any detectable release of cAMP above the inaccuracy of measurement. A standard procedure for measuring cAMP release is described in the examples and may be used for determining a significant or non-significant release of cAMP. The "release of cAMP" refers to an intracellular release of cAMP and/or an extracellular release or secretion of cAMP, preferably only to a secretion of cAMP. cAMP refers to cyclic adenosine monophosphate which acts as a second messenger molecule in cellular signal transduction. cAMP is synthesized in cells from ATP by the adenylyl cyclase. A biological process or signal transduction pathway which is "independent of cAMP signaling" preferably does not involve activation of adenylyl cyclase.

"Sex steroids", also known as gonadal steroids or sex hormones, in particular refer to steroid hormones that interact with vertebrate androgen or estrogen receptors. The term "sex steroid" includes androgens such as anabolic steroids, androstenedione, dehydroepiandrosterone, dihydrotestosterone and testosterone; estrogens such as estradiol, estriol and estrone; and progesterone. Preferably, sex steroids refer to naturally occurring sex steroids, more preferably to natural human sex steroids.

Preferred sex steroids according to the invention are estradiol and progesterone, in particular progesterone.

The present invention is according to one aspect based on the finding that an improved recombinant FSH preparation having an optimal glycosylation pattern is capable of inducing secretion of sex steroids such as progesterone at low FSH concentrations at which no significant cAMP release is induced. In particular, in this certain aspect the improved FSH according to the present invention induces sex steroid secretion at much lower concentrations than the commonly used urinary FSH or recombinant FSH obtained from CHO cells. Thereby, the improved FSH can be administered at much lower doses which reduces the risk of adverse effects and furthermore lowers the production costs. Furthermore, if given at comparable doses, in this embodiment the improved FSH provides a longer activity in the patient's body compared to the commonly used FSH, since also a long time after administration when only a very low concentration of the FSH remains in the circulation, the FSH according to this embodiment of the present invention still exerts its biological activity and preferably, stimulates or co-stimulates germ cell maturation and/or the release of sex steroids. Moreover, at high concentrations, the improved FSH according to the present invention and the commonly used urinary or CHO-derived FSH show comparable effects. Therefore, there is no additional risk of overdosing compared to the commonly used FSH.

Furthermore, the present inventors have demonstrated in cynomolgus monkeys that the improved FSH according to the present invention has a similar or even higher pharmacological effect when compared to the commonly used urinary or CHO-derived FSH. This is in particular surprising since the FSH according to the present invention shows in rats and monkeys a lower maximum serum concentration (Cmax) and circulation half-life than the common FSH preparations obtained from urine or CHO cells. Since in spite of the lower bioavailability the improved FSH has a similar or higher pharmacological effect, it can be concluded that the improved FSH according to the present invention has a higher specific therapeutic activity than the urinary or CHO-derived FSH. According to obtained clinical data, in humans the improved FSH according to the present invention has a significantly higher Cmax than the common FSH preparations; however, the circulation half-life is slightly lower but comparable for the improved FSH. Most surprising, the improved FSH preparations according to the present invention showed therapeutic effects in humans, in particular follicular growth, even after administration of only a single dose. In contrast, no effects can be observed after single dose administration of the commonly used FSH preparations. Therefore, it is expected that with the improved FSH a much more precise treatment of the patients is possible. In particular, it is possible to use exactly timed and sized doses to treat and especially improve fertility of the patient and potentially a lengthy continuous treatment is not necessary. Thereby, also the risk of multiple pregnancies is reduced.

In summary, the improved FSH preparations according to the present invention are more effective. Therefore, smaller doses can be administered to the patient, which causes less adverse effects, is more convenient for the patient and is less cost intensive. Furthermore, a more specific and detailed dosage regimen is possible with the improved FSH. Furthermore, the reduced half-life reduces unwanted side effects and furthermore provides a faster removal of the FSH from the human body after termination of the therapy.

Without being bound to this theory, the present inventors assume that the higher specific therapeutic activity of the FSH preparations according to the present invention is based on the improved glycosylation pattern. In particular, the high amount of bisecting GlcNAc residues and/or the high amount of 2,6-coupled sialic acids as well as the high amount of sulfated glycans may be responsible for the high activity. Furthermore, the FSH preparations according to the present invention also show a much more diverse and complex glycosylation pattern, meaning that more different glycan structures are present in the preparation compared to conventional FSH preparations obtained e.g. from CHO cells. It is believed that the CHO-derived FSH is only able to activate one single pathway in the target cells while the improved FSH according to the present invention, due to its unique glycosylation pattern, apparently exerts its biological activity via multiple different pathways, resulting in an increased biological response. As shown by the experimental data herein, some of these pathways involve cAMP signaling while other, novel pathways are cAMP independent.

In view of these findings, the present invention provides, in a first aspect, a FSH preparation, wherein the FSH in the preparation has a glycosylation pattern comprising one or more of the following characteristics:
  (i) a relative amount of glycans carrying bisecting N-acetylglucosamine (bisGlcNAc) of at least 20%; and/or
  (ii) a relative amount of glycans carrying fucose of at least 30%; and/or
  (iii) a relative amount of 2,6-coupled sialic acid of at least 30%; and/or
  (iv) it is a diverse glycosylation pattern.

In certain embodiments, the present invention provides a FSH preparation, wherein the FSH in the preparation has a glycosylation pattern comprising one or more of the following characteristics:
  (i) a relative amount of glycans carrying bisecting N-acetylglucosamine (bisGlcNAc) of at least 35%;
  (ii) a relative amount of glycans carrying fucose of at least 60%; and
  (iii) a relative amount of 2,6-coupled sialic acid of at least 30%.

Preferably, said FSH is a recombinant FSH and thus, is obtained by recombinant production in a host cell, which preferably is a human host cell. Suitable human host cells which provide a respective glycosylation pattern are described subsequently.

Preferably, the glycosylation pattern comprises at least two of the features (i), (ii) and (iii) (in particular features (i) and (ii), (i) and (iii), or (ii) and (iii)), and more preferably all of the features (i), (ii) and (iii). Furthermore, the glycosylation pattern may further comprise a relative amount of at least tetraantennary glycans of at least 15%, and/or a relative amount of glycans carrying one or more sialic acid residues of at least 80%, and/or a relative amount of glycans carrying galactose of at least 95%, and/or a relative amount of glycan branches carrying a terminal galactose unit of at least 60%, and/or a relative amount of glycans carrying a sulfate group of at least 1%, preferably at least 2.5%. The terminal galactose unit may optionally further carry a sialic acid residue. The recombinant FSH in the composition preferably has a Z-number of at least 200.

The relative amount of glycans carrying bisGlcNAc is preferably at least 25%, at least 27%, at least 30%, at least 35%, at least 38% or at least 40%. More preferably, it is in the range of from about 25% to about 60%. in particular in the range of from about 35% to about 60% or in the range of from about 38% to about 50% or in the range of from about 40% to about 45%. According to one embodiment, it is about 42%. The relative amount of glycans carrying one or more sialic acid residues is preferably at least 83%, at least 85% or at least 88%, and more preferably in the range of from about 85% to about 98% or in the range of from about 88% to about 95%, most preferably about 90%. The Z-number is preferably at least 210. more preferably at least 215, at least 220, at least 230 or at least 240. A higher Z-number is for example obtainable by enriching the FSH preparation for acidic and/or negatively charged FSH proteins. Preferably, the relative amount of at least tetraantennary glycans is at least 16%, at least 17%, at least 18% or at least 19%, more preferably at least 20% or at least 21%. The relative amount of at least triantennary glycans, in particular tri- and tetraantennary glycans, preferably is at least 25%, at least 30%, at least 35% or at least 40%, more preferably at least 45%, at least 50% or at least 55%. Preferably, the relative amount of glycans carrying fucose is at least 35%, at least 40%, at least 50%, at least 60% or at least 70%, more preferably at least 75% or at least 78%. It may be in the range of from about 70% to about 90%, in particular in the range of from about 75% to about 85%. Preferably, the relative amount of 2,6-coupled sialic acid is at least 40%, at least 45%, at least 50%, at least 53%, at least 55%, at least 60% or at least 65%, in particular in the range of about 40% to about 99%, preferably about 40% to about 80%, about 50% to about 60% or about 53% to about 70%. Preferably, the ratio of 2,3-coupled sialic acid to 2,6-coupled sialic acid is in the range of from about 1:10 to about 7:3, more preferably from about 1:5 to about 3:2 or from about 1:2 to about 1:1, most preferably from about 2:3 to about 1:1. In preferred embodiments, the relative amount of 2,6-coupled sialic acids exceeds that of 2,3-coupled sialic acids. The relative amount of glycans carrying galactose preferably is at least 97% and most preferably is about 98%. Preferably, the relative amount of glycan branches carrying a galactose unit optionally modified by a sialic acid residue is at least 65%, more preferably at least 70% or at least 73%. It is preferably in the range of from about 60% to about 95%, and more preferably in the range of from about 70% to about 80%. Preferably, the relative amount of glycans carrying a sulfate group (sulfated glycans) is at least 1%, at least 1.5%, at least 2%, at least 2.5%, at least 3% or at least 5%, more preferably at least 7%, at least 10% or at least 12%.

According to one embodiment, the relative amount of glycans carrying a sulfate group does not exceed 50%, preferably 40%, 35%, 30%, 25% or 20%.

In preferred embodiments, the FSH in the preparation has a diverse glycosylation pattern wherein the FSH in the preparation comprises at least 45 or preferably at least 50 different glycan structures, wherein each one of the different glycan structures has a relative amount of at least 0.05% of the total amount of glycan structures of the FSH in the preparation. According to one embodiment, the FSH in the preparation comprises at least 35 or preferably at least 40 different glycan structures, wherein each one of the different glycan structures has a relative amount of at least 0.1% of the total amount of glycan structures of the FSH in the preparation; and/or the FSH in the preparation comprises at least 20 or preferably at least 25 different glycan structures, wherein each one of the different glycan structures has a relative amount of at least 0.5% of the total amount of glycan structures of the FSH in the preparation. In a further embodiment, the FSH in the preparation comprises at least 40%, preferably at least 50% more different glycan structures than FSH obtained from CHO cells in a corresponding preparation, wherein each one of the different glycan structures has a relative amount of at least 0.05%, 0.1% or 0.5% of the total amount of glycan structures of the FSH in the respective preparation.

In preferred embodiments, the recombinant FSH preparation according to the invention does not comprise N-glycolyl neuraminic acids (NeuGc) or detectable amounts of NeuGc. Furthermore, the recombinant FSH preparation according to the invention preferably also does not comprise Galili epitopes (Galα1,3-Gal structures) or detectable amounts of the Galili epitope.

The present invention in particular provides a FSH with a human glycosylation pattern. Due to these glycosylation properties, foreign immunogenic non-human structures which induce side effects are absent which means that unwanted side effects or disadvantages known to be caused by certain foreign sugar structures such as the immunogenic non-human sialic acids (NeuGc) or the Galili epitope (Gal-Gal structures), both known for rodent production systems, or other structures like immunogenic high-mannose structures as known from e.g. yeast systems are avoided.

In certain embodiments the glycosylation pattern of the recombinant FSH in the preparation according to the present invention comprises one or more, preferably all of the following characteristics:

(i) a relative amount of glycans carrying bisecting N-acetylglucosamine (bisGlcNAc) in the range of from about 25% to about 50%;

(ii) a relative amount of glycans carrying fucose of at least 35%;

(iii) a relative amount of 2,6-coupled sialic acid of at least 53%;

(iv) a relative amount of glycans carrying one or more sialic acid residues of at least 88%; and (v) a relative amount of at least tetraantennary glycans of at least 16%.

In certain preferred embodiments, the recombinant FSH preparation according to the invention has one of the glycosylation patterns listed in the following Table 1:

TABLE 1

Specific glycosylation parameters

| Embodiment | B | 2,8-S | sulfate | S > 0 | 2 | tetra |
|---|---|---|---|---|---|---|
| 1 | ≥20 | ≥53 | ≥2.5 | | | |
| 2 | ≥20 | ≥53 | ≥2.5 | ≥80 | ≥200 | ≥15 |
| 3 | ≥20 | ≥53 | ≥2.5 | ≥85 | | |
| 4 | ≥20 | ≥53 | ≥2.5 | | ≥220 | |
| 5 | ≥20 | ≥53 | ≥2.5 | | | ≥17 |
| 6 | ≥20 | ≥53 | ≥2.5 | ≥85 | ≥220 | ≥17 |
| 7 | 20-50 | ≥53 | ≥2.5 | | | |
| 8 | ≥20 | 53-80 | ≥2.5 | | | |
| 9 | ≥20 | ≥53 | 2.5-30 | | | |
| 10 | ≥20 | ≥53 | ≥2.5 | ≥80 | 200-260 | ≥15 |
| 11 | ≥20 | ≥53 | ≥2.5 | ≥80 | ≥200 | 15-30 |
| 12 | 20-50 | 53-80 | 2.5-30 | 80-100 | 200-260 | 15-30 |
| 13 | ≥25 | ≥55 | ≥3 | | | |
| 14 | ≥30 | ≥55 | ≥3 | | | |
| 15 | ≥25 | ≥60 | ≥3 | | | |
| 16 | ≥25 | ≥55 | ≥10 | | | |
| 17 | ≥30 | ≥60 | ≥10 | | | |
| 18 | ≥25 | ≥55 | ≥3 | ≥80 | ≥200 | ≥15 |
| 19 | ≥25 | ≥55 | ≥3 | ≥85 | ≥220 | ≥17 |
| 20 | ≥30 | ≥60 | ≥10 | ≥85 | ≥220 | ≥17 | shown are the relative amounts of glycans having the following property:
B: bisecting GlcNAc; 2,6-S: 2,6-coupled sialic acid; sulfate: sulfated glycans; S > 0: at least one sialic acid; Z: Z number; tetra: at least tetraantennary glycans In embodiments 1 to 12 listed in table 1, preferably the relative amount of bisecting GlcNAc is at least 25% instead of at least 20%; and/or the relative amount of 2,6-coupled sialic acids preferably is at least 55%, more preferably at least 60%, instead of at least 53%; and/or the relative amount of sulfated glycans preferably is at least 3%. more preferably at least 10%, instead of at least 2.5%. The glycosylation patterns listed in table 1 preferably are human glycosylation patterns and/or do not comprise NeuGc and the Galili epitope.

Furthermore, the present invention provides a recombinant FSH preparation that is obtainable by production in a human host cell or a human cell line. Preferably, the recombinant FSH is obtainable from a human myeloid cell line, preferably an immortalized human myeloid leukemia cell line, in particular the cell line GT-5s or a cell line derived therefrom or a cell line homologous to GT-5s. It was found that an FSH produced in said cell line exhibits a glycosylation pattern as described above and in particular exhibits the advantageous therapeutic and pharmacological effects described herein. Thus, the present invention also pertains to a method for producing a recombinant FSH preparation by recombinantly expressing the FSH in a suitable cell line, in particular a cell line as described above, preferably the cell line GT-5s, a cell line derived from GT-5s or a cell line homologous to GT-5s. The recombinant FSH respectively produced can be isolated and optionally purified.

Thus, the recombinant FSH preparation preferably is obtainable by a process comprising the steps of:
(i) cultivating a human host cell, preferably derived from the cell line GT-5s or a homologous cell line, comprising nucleic acids coding for the FSH alpha and beta subunits under conditions suitable for expression of the FSH; and
(ii) isolating FSH.

The human host cells used for expression preferably are myeloid cells, in particular immortalized myeloid leukemia cells, and preferably are or are derived from the cell line GT-5s or is a cell line homologous thereto. The human host cells are cultured so that they express FSH. Suitable culture conditions are known to the skilled person.

The isolation of FSH preferably comprises the further steps of:
(a) obtaining the culture supernatant where the FSH is secreted by the human cells, or lysing the human cells where the FSH is not secreted;
(b) isolating the FSH from the culture supernatant or cell lysate using chromatographic steps such as reversed phase chromatography, size exclusion chromatography and/or hydrophobic interaction chromatography; and
(c) optionally obtaining an acidic fraction of the FSH by removing basic FSH isoforms, preferably by using anion exchange chromatography including a washing step which removes basic FSH isoforms, such as a washing step at about pH 5.0 or about pH 4.5 or about pH 4.0.

Preferably, the nucleic acid coding for the FSH alpha subunit and the nucleic acid coding for the FSH beta subunit are comprised in expression cassettes comprised in a suitable expression vector that allows the expression in a human host cell. The nucleic acid coding for the FSH alpha subunit and the nucleic acid coding for the FSH beta subunit may be comprised in the same vector, but preferably are comprised in separate vectors. Furthermore, they may also be expressed from one expression cassette using appropriate elements such as an IRES element. Preferably, the FSH is secreted by the human cells. In preferred embodiments, cultivation of the human cells is performed in a fermenter and/or under serum-free conditions.

A suitable purification process for the recombinant FSH is described, for example, in the U.S. patent application no. US 61/263,931, the European patent application no. EP 09 014 585.5 and the PCT patent application no. WO 2011/063943.

The recombinant FSH preparation obtainable by production in human host cells or a human cell line preferably exhibits the features described herein with respect to the recombinant FSH preparation according to the present invention. In particular, its glycosylation pattern comprises one or more of the characteristics described above, preferably at least one glycosylation pattern as described in Table 1 and/or in claims 1 to 6.

In preferred embodiments of the aspects of the present invention, the recombinant FSH according to the present invention is recombinant human FSH (rhFSH), preferably obtainable by production in a human cell line, such as the cell line GT-5s, which comprises one or more nucleic acids encoding the human FSH subunits and elements for expressing said one or more nucleic acids in the host cell. Preferably, the alpha subunit of the rhFSH has the amino acid sequence according to SEQ ID NO: 1 or an amino acid sequence having a homology or preferably identity to SEQ ID NO: 1 over its entire length of at least 80%, preferably at least 85%, at least 90%, at least 95% or at least 98%. In preferred embodiments, the alpha subunit of the rhFSH comprises asparagine residues at positions 52 and 78 and is glycosylated at amino acids Asn52 and Asn78. The beta subunit of the rhFSH preferably has the amino acid sequence according to SEQ ID NO: 2 or an amino acid sequence having a homology or preferably identity to SEQ ID NO: 2 over its entire length of at least 80%, preferably at least 85%, at least 90%, at least 95% or at least 98%. In preferred embodiments, the beta subunit of the rhFSH comprises asparagine residues at positions 7 and 24 and is glycosylated at amino acids Asn7 and Asn24.

According to one embodiment, the recombinant FSH preparation according to the present invention is capable of stimulating the release of progesterone in granulosa cells (a) at concentrations where no significant amounts of cAMP are released; and/or
(b) by inducing a signal transduction pathway which is independent of cAMP signaling.

According to one embodiment, the recombinant FSH preparation according to the present invention is capable of stimulating or co-stimulating germ cell maturation by a biological process which is independent of cAMP signaling. It was surprisingly found in experiments that the glycosylation pattern described above results in a respective novel pharmacological profile of the recombinant FSH, which exhibits the pharmacological and therapeutic advantages described herein.

The recombinant FSH preparation according to the present invention may have one or more of the subsequently described characteristics as can be determined in a granulose cell assay (as is e.g. described in Example 2). As is demonstrated by the examples, the recombinant FSH having the above described glycosylation pattern and in particular the recombinant FSH obtainable by production in the cell line GT-5s exhibit the subsequently described characteristics which result in the pharmacological and therapeutic advantages described herein.

The recombinant FSH preparation is according to one embodiment capable of stimulating the release of progesterone in granulose cells at concentrations which are below the minimum concentration needed for the induction of cAMP release by the granulose cells. The release of progesterone, estradiol and/or cAMP mentioned below refers to an in vitro release in about $1*10^4$ to about $1*10^6$ granulosa cells/ml, preferably in about $5*10^4$ to about $1*10^5$ granulosa cells/ml, in particular under conditions as described in example 2, below.

Preferably, the recombinant FSH preparation according to the present invention is capable of releasing at least 100 ng/ml, at least 150 ng/ml, at least 200 ng/ml, preferably at least 250 ng/ml, at least 300 ng/ml or at least 400 ng/ml progesterone at a concentration which does not induce a cAMP release or which induces a cAMP release of less than 20 pmol/ml, less than 15 pmol/ml, less than 10 pmol/ml, less than 5 pmol/ml.

Furthermore, the recombinant FSH preparation according to the present invention is preferably capable of releasing at least 100 ng/ml, at least 200 ng/ml, preferably at least 300 ng/ml or at least 400 ng/ml progesterone at a FSH concentration that is lower than the concentration necessary with human urinary FSH or recombinant FSH produced in CHO cells (Gonal F). Thus, it is preferably capable of releasing at least 100 ng/ml, at least 200 ng/ml, preferably at least 300 ng/ml or at least 400 ng/ml progesterone at a concentration wherein human urinary FSH or recombinant FSH produced in CHO cells (Gonal F) do not result in a corresponding, respectively equally high release of progesterone. As is demonstrated by the examples, the recombinant FSH according to the present invention induces respectively stimulates the production of progesterone more strongly than human urinary FSH or recombinant FSH produced in CHO cells (Gonal F).

Furthermore, the recombinant FSH preparation according to the present invention is preferably capable of releasing at least 50 nmol/l, at least 75 nmol/l, at least 100 nmol/l, at least 125 nmol/l or at least at least 150 nmol/l estradiol at a FSH concentration which does not induce a cAMP release or which induces a cAMP release of less than 20 pmol/ml, less than 15 pmol/ml, less than 10 pmol/ml, less than 5 pmol/ml.

Furthermore, the recombinant FSH preparation according to the present invention is preferably capable of releasing at least 50 nmol/l, at least 75 nmol/l, at least 100 nmol/l, at least 125 nmol/l, at least 150 nmol/l, at least 200 nmol/l, at least 250 nmol/l, at least 300 nmol/l or at least 350 nmol/l estradiol at a FSH concentration that is lower than the concentration necessary with human urinary FSH or recombinant FSH produced in CHO cells (Gonal F). Thus, it is preferably capable of releasing at least 50 nmol/l, at least 75 nmol/l, at least 100 nmol/l, at least 125 nmol/l, at least at least 150 nmol/l, at least 200 nmol/l, at least 250 nmol/l, 300 nmol/l or at least 350 nmol/l estradiol at a concentration wherein human urinary FSH or recombinant FSH produced in CHO cells (Gonal F) does not result in a corresponding, respectively equally high release of estradiol. As is demonstrated by the examples, the recombinant FSH preparations according to the present invention induce respectively stimulate the production of estradiol more strongly than human urinary FSH or recombinant FSH produced in CHO cells (Gonal F).

The respective characteristics described herein on the cAMP release and the expression of the sex steroids can be analysed and determined by using a granulose cell assay, as is e.g. described in example 2.

The recombinant FSH preparation according to the present invention preferably is present in a pharmaceutical composition. Thus, another aspect of the present invention is a pharmaceutical composition comprising the recombinant FSH preparation according to the present invention for use in infertility treatment as defined herein. The pharmaceutical composition may include further pharmaceutically active agents, in particular further agents useful in infertility treatment such as other gonadotropins, in particular LH and/or CG, preferably recombinant and/or human LH or CG. Alternatively, the pharmaceutical composition comprising the recombinant FSH may be designed for use in combination with such further pharmaceutically active agents.

Furthermore, the present invention provides the recombinant FSH preparation according to the present invention or the pharmaceutical composition according to the present invention for use in infertility treatment as well as a method for treatment of infertility comprising the administration of the recombinant FSH preparation according to the present invention or the pharmaceutical composition according to the present invention to the patient.

As discussed above, in certain embodiments the recombinant FSH preparation according to the present invention is capable of stimulating or co-stimulating the release of sex steroids such as progesterone, in particular the release of progesterone in granulosa cells, already at concentrations where no significant amount of cAMP is released. In particular, the recombinant FSH according to the present invention may be capable of stimulating release of sex steroids such as progesterone in granulosa cells at concentrations which are below the minimum concentration needed for the induction of cAMP release by the granulosa cells.

Furthermore, in certain embodiments the recombinant FSH preparation according to the present invention is capable of stimulating release of progesterone, in particular release of progesterone in granulosa cells, by inducing a signal transduction pathway which is independent of cAMP signaling. Preferably, the infertility treatment includes the induction of a signal transduction pathway which is independent of cAMP signaling by the recombinant FSH according to the present invention, resulting in the stimulation of progesterone release. However, other signal transduction pathways including cAMP signaling may additionally be activated by the recombinant FSH. In other embodiments, the infertility treatment does not involve the induction of a significant release of cAMP by the recombinant FSH according to the present invention.

In further embodiments, as described above, the recombinant FSH preparation according to the present invention is capable of stimulating or co-stimulating germ cell maturation by a biological process which is independent of cAMP signaling.

Thus, the present invention also pertains to the recombinant FSH preparation or the pharmaceutical composition described above for inducing and/or stimulating the secretion of sex steroids also independent of cAMP. Furthermore, the present invention also pertains to the recombinant FSH preparation or the pharmaceutical composition described above for stimulating or co-stimulating germ cell maturation by a biological process which is independent of cAMP signaling. Additionally, the present invention also pertains to the recombinant FSH preparation or the pharmaceutical composition described above for inducing and/or stimulating the secretion of sex steroids at FSH concentrations at which no significant cAMP release is induced. Furthermore, the present invention also pertains to the recombinant FSH preparation or the pharmaceutical composition described above for inducing sex steroid secretion at much lower concentrations than the commonly used urinary FSH or recombinant FSH obtained from CHO cells. The pharmacological and therapeutic advantages of the respective uses in particular for infertility treatment were discussed in detail above.

In particular, the infertility treatment may include the stimulation or co-stimulation of germ cell maturation by a biological process which is independent of cAMP signaling. However, the infertility treatment may additionally comprise the stimulation of germ cell maturation by one or more other biological processes which involve cAMP signaling. In other embodiments, the infertility treatment does not involve the stimulation of germ cell maturation by such other biological processes.

The germ cell maturation preferably includes follicular growth and/or spermatogenesis. Furthermore, the biological process by which the FSH stimulates germ cell maturation may include secretion of sex steroids, in particular progesterone, preferably by granulosa cells. Preferably, the biological process which is independent of cAMP signaling refers to the secretion of sex steroids, in particular progesterone, preferably by granulosa cells, induced by a signal transduction pathway which does not involve cAMP as messenger molecule.

In preferred embodiments, the recombinant FSH preparation according to the invention is capable of eliciting a biological effect even after the administration of only a single dose. In particular, the FSH preparation according to the invention or the pharmaceutical composition according to the invention is capable of inducing follicular growth and/or ovular maturation in a patient, in particular a human patient, after administration of only a single dose of the FSH preparation or pharmaceutical composition. Preferably, the biological effect achieved after the administration of only a single dose is higher, in particular the follicular growth and/or ovular maturation, is more pronounced and/or is achieved in a higher ratio of the treated patients compared to FSH preparations obtained from human urine and/or expressed in CHO cells. Said single dose in particular comprises at least 10 IU FSH, preferably at least 15 IU FSH, at least 20 IU FSH or at least 25 IU FSH, and/or 1000 IU FSH or less, preferably 750 IU FSH or less, 500 IU FSH or less, 300 IU FSH or less, 200 IU FSH or less, 150 IU FSH or less, 100 IU FSH or less or 50 IU FSH or less. Preferably, said single dose comprises about 10 IU to about 500 IU FSH, more preferably about 20 IU to about 300 IU FSH, for example about 25 IU FSH, about 75 IU FSH or about 100 IU FSH.

In further embodiments, the recombinant FSH preparation according to the invention has a lower circulation half-life than FSH preparations obtained from human urine and/or expressed in CHO cells. In particular, it has a lower circulation half-life in one or more of humans, cynomolgus monkeys, rats and/or mice. Preferably, the circulation half-life is at least 5% lower, more preferably at least 10%, at least 15% or at least 20% lower than that of FSH preparations obtained from human urine and/or expressed in CHO cells. In certain embodiments, the recombinant FSH preparation according to the invention has a lower bioavailability than FSH preparations obtained from human urine and/or expressed in CHO cells, in particular, in one or more of humans, cynomolgus monkeys, rats and/or mice. Preferably, the bioavailability is at least 5% lower, more preferably at least 10%, at least 15% or at least 20% lower than that of FSH preparations obtained from human urine and/or expressed in CHO cells. Bioavailability in this respect preferably refers to the area under the curve (AUC) value obtained in pharmacokinetic studies wherein the serum FSH concentration is determined at different time points after administration of a defined amount of FSH. Circulation half-life and bioavailability preferably are determined after administration of the FSH by subcutaneous injection, in particular after single dose administration, wherein the single dose preferably comprises about 10 to about 1000 IU FSH, more preferably about 25 IU to about 500 IU FSH or about 50 IU to about 300 IU FSH, in particular about 100 IU FSH. In particular, circulation half-life and bioavailability are determined as disclosed in Example 6, below.

In preferred embodiments, the recombinant FSH preparation according to the invention has a therapeutic efficacy which is similar to or even higher than that of FSH preparations obtained from human urine and/or expressed in CHO cells, in particular, in one or more of humans, cynomolgus monkeys, rats and/or mice. The term "therapeutic efficacy" preferably refers to the ability to stimulate release of estradiol and/or inhibin-B when administered to a subject. The therapeutic efficacy is determined preferably by measuring the estradiol and/or inhibin-B concentration in the blood or serum of one or more subjects after administration of the FSH by subcutaneous injection, in particular after single dose administration, wherein the single dose preferably comprises about 10 to about 1000 IU FSH, preferably about 25 IU to about 500 IU FSH or about 50 IU to about 300 IU FSH, in particular about 100 IU FSH. In particular, the therapeutic efficacy is determined as disclosed in Example 5, below. Similar therapeutic efficacies in particular refer to stimulations of estradiol and/or inhibin-B release by the respective FSH preparations which result in estradiol and/or inhibin-B serum concentrations which differ from each other by no more than 25%, preferably no more than 20%, no more than 15% or no more than 10%.

The FSH preparation obtained from human urine in particular is obtained from urine of post-menopause women. The FSH preparation expressed in CHO cells is for example expressed in the CHO cell line CHOdhfr- [ATCC No. CRL-9096]. The FSH preparation obtained from human urine and the FSH preparation expressed in CHO cells preferably are commercially available and approved pharmaceutical preparations, in particular Bravelle and Gonal-f, respectively. When comparing the effects of different FSH preparations, in particular their circulation half-life, bioavailability and therapeutic efficacy, the FSH preparations are analyzed by administering them to similar subject groups with the same dosage regimen using the same administration pathway and using similar or the same further conditions.

In certain embodiments, the recombinant FSH preparation according to the present invention is administered to the patient in a dose which results in an FSH concentration in the circulation of the patient of less than 5 IU/L. In certain embodiments, the dose to be administered to the patient results in an FSH concentration in the circulation of the patient which is less than about 4 IU/L, in particular less than about 3 IU/L, less than about 2 IU/L, less than about 1 IU/L or less than about 0.5 IU/L. The concentration of the FSH in the patient's circulation for example is in the range of about 0.01 to about 5 IU/L, in particular about 0.05 to about 2 IU/L, about 0.1 to about 1.5 IU/L or about 0.2 to about 1 IU/L. In particular, the FSH is administered to the patient in a dose which does not induce a significant release of cAMP. As demonstrated in the examples, the recombinant FSH preparations according to the invention in certain embodiments elicit a therapeutic effect at these concentrations. However, the recombinant FSH preparations according to the invention may also be administered in a dose which results in higher FSH concentrations in the patient's circulation.

In preferred embodiments, the infertility treatment includes assisted reproductive technologies, ovulation induction, in-vitro fertilization, for example in-vitro fertilization with intracytoplasmic sperm injection, gamete intrafallopian transfer, intrauterine insemination, treatment of anovulatory disorder in women, treatment of severe hormone deficiency disorder for egg maturation in woman, treatment of sperm production deficiencies in men, and/or the enablement or improvement of germ cell maturation such as folliculogenesis and spermatogenesis, in particular follicle maturation in women, for example during in vitro fertilization stimulation protocols and/or for anovulatory disorder treatment.

Preferably, the recombinant FSH preparation according to the present invention is for parenteral administration to the patient. In particular, the recombinant FSH is to be administered by injection or infusion, for example intravenously, intramuscularly or subcutaneously. In certain embodiments of the present invention, the recombinant FSH is present in a pharmaceutical composition. Suitable dosage regiments can be determined by the skilled artisan and can be derived from the general knowledge in the field.

The pharmaceutical composition according to the invention may be in the form of a single unit dose or a multiple unit dose. Preferably, the pharmaceutical composition is a sterile solution comprising the recombinant FSH according to the present invention, further comprising one or more ingredients selected from the group consisting of solvents such as water, buffer substances, stabilizers, preservatives, excipients, surfactants and salts. A single unit dose preferably comprises about 10 IU to about 750 IU FSH, more preferably about 25 IU to about 500 IU FSH, about 50 IU to about 400 IU FSH, or about 100 IU to about 300 IU FSH. A multiple unit dose comprises enough FSH to provide for multiple single doses, in particular at least 5, at least 10, at least 20 or at least 50 single doses. The pharmaceutical composition may for example be in the form of an injection pen.

FIGURES

FIG. 10 shows schematic drawings of complex-type glycan structures which may be attached to the FSH glycosylation sites. Shown are (a) biantennary, (b) triantennary and (c) tetraantennary structures. One or more of the sialic acid and galactose residues may also be absent in these structures and the structures may further comprise, for example, a bisecting GlcNAc residue, a fucose residue and/or sulfate groups. Sia: sialic acid: Gal: galactose, also referred to herein as terminal galactose; GlcNAc: N-acetylglucosamine; Man: mannose.

EXAMPLES

Example 1

Preparation of FSH (Invention)

FSH is produced by cultivation of GT-5s cells stably transfected with two expression constructs harbouring the alpha and beta chain of human FSH (alpha chain accession number NT_007299.13; beta chain accession number NT_009237.18). The plasmid for the expression of the FSH alpha chain is carrying the gene of a mutated version of the murine dihydrofolate reductase (dhfr) with higher resistance to the enzyme inhibitor methotrexate than the native form and the second plasmid for the expression of the FSH alpha chain is carrying the puromycin resistance gene.

Transfection of the cell line for FSH (invention) expression was performed by nucleofection using the two expression plasmids described above. For selection and amplification of stable antibody producing cell clones puromycin and methotrexate were added at increasing concentrations. Amplified cell pools were seeded in a semi-solid matrix for single cell cloning by the Clone PixFL technology or single cell cloning by limited dilution. The clones were screened for high secretion of intact FSH molecules.

FSH is produced by fermentation of the final FSH producing GT-5s clone in batch, fed-batch or perfusion process under serum free conditions. The fermentation is usually run for 2-3 weeks.

After fermentation the supernatant is filtered through 2 μm filters to eliminate cells and cell debris prior to a sterile filtration step using 0.2 μm filters. The purification process utilizes a reverse phase chromatography (RPC) as capture step followed by a concentration step and a subsequent size exclusion chromatography (SEC). Optionally, the eluate is then applied to an anion exchange chromatography (AEC) to eliminate the less acidic FSH contents. This is done by washing the bound FSH with washing buffer at pH 5.0 ("enrichment at pH 5.0") or pH 4.5 ("enrichment at pH 4.5") to elute less acidic FSH isoforms prior to elution of the desired FSH fraction. As a polishing step a hydrophobic interaction chromatography (HIC) is used to gain FSH at high purity.

Example 2

Granulosa Cell Assay

Figure 1:
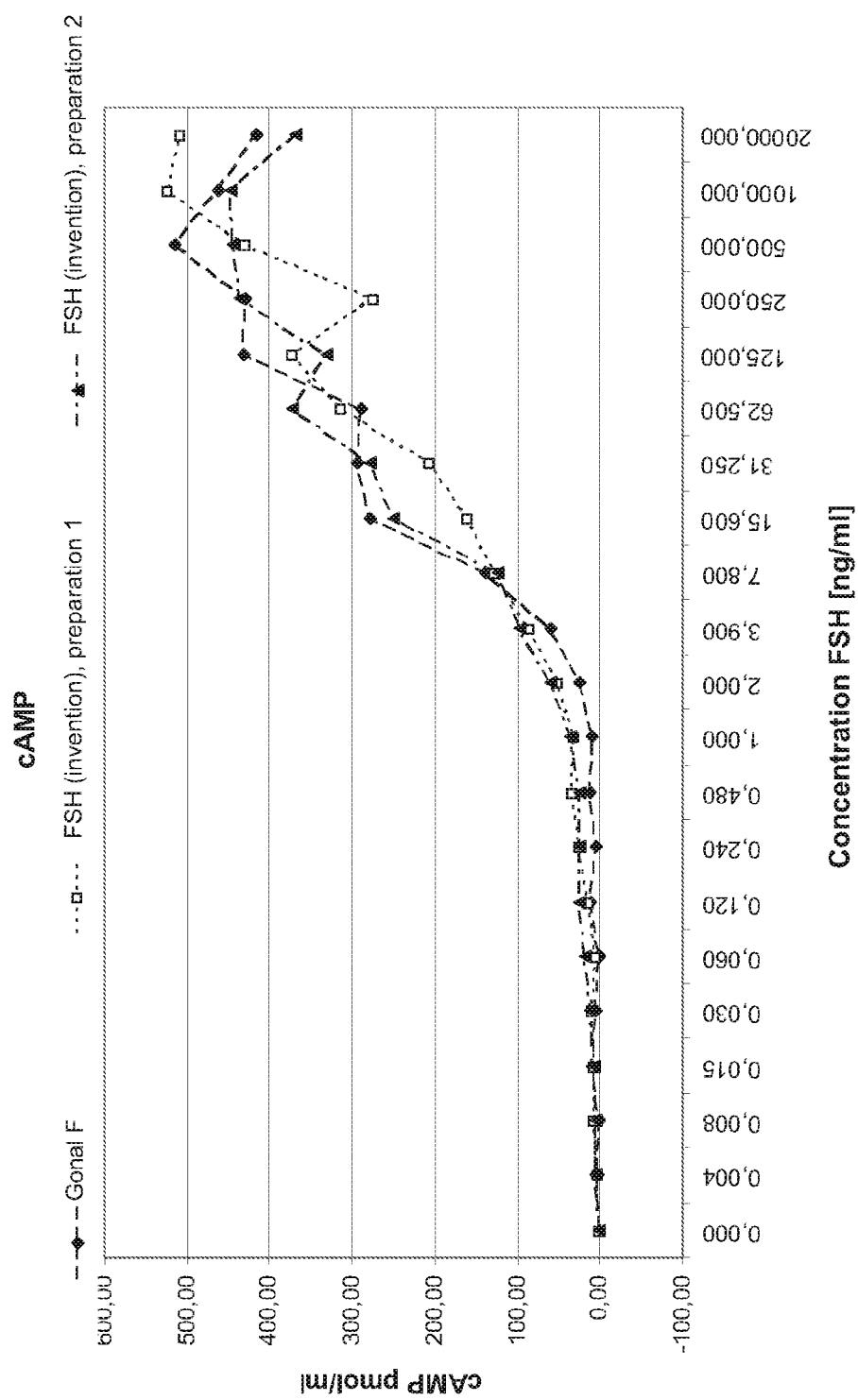
FIG. 1 shows the cAMP release of isolated granulosa cells stimulated with different concentrations of the improved recombinant human FSH (FSH (invention); preparation 1: open squares, preparation 2: closed triangles) or FSH obtained from CHO cells (Gonal F; closed diamonds).
Figure 2:
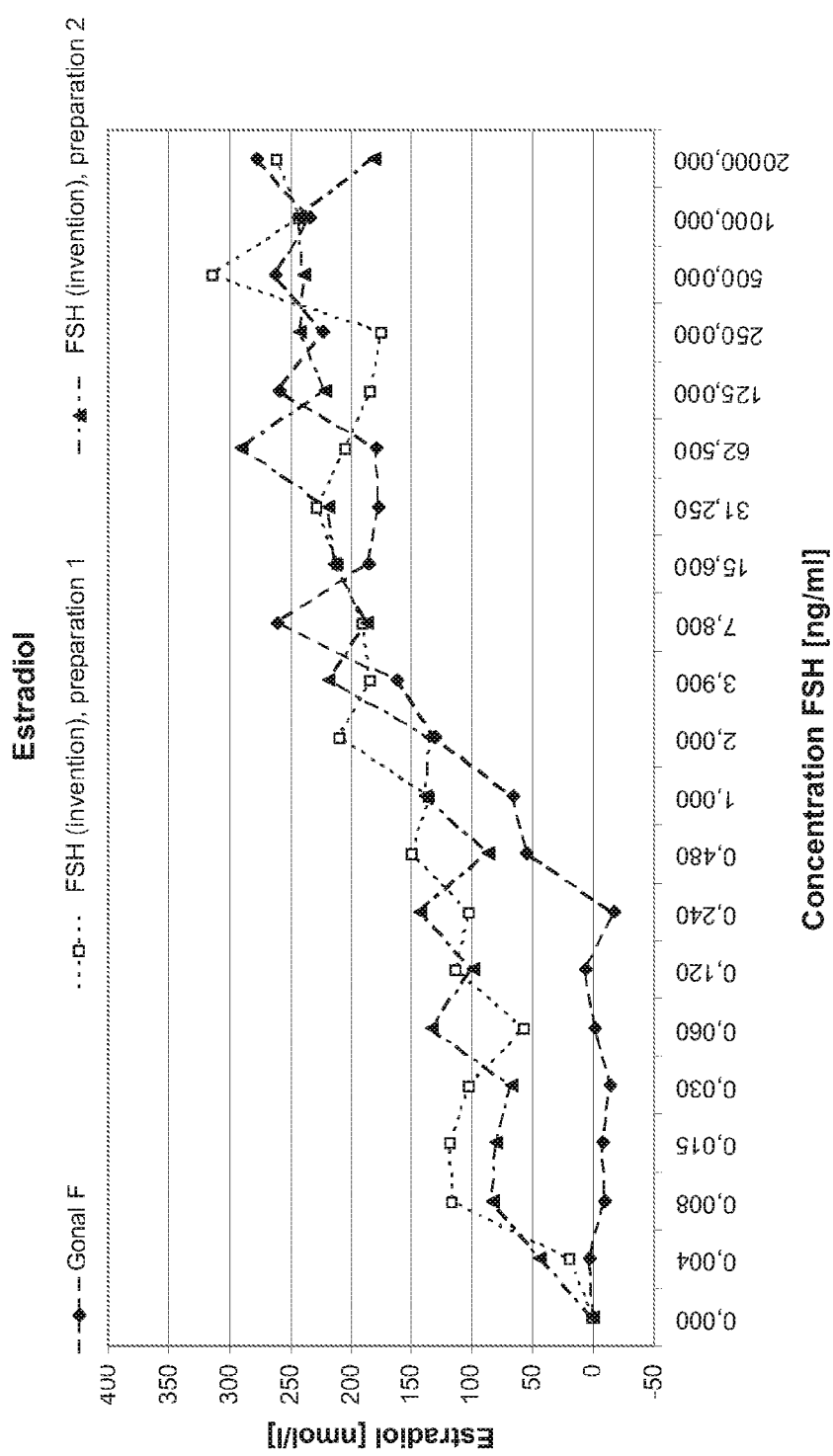
FIG. 2 shows the estradiol synthesis of isolated granulosa cells stimulated with different concentrations of the improved recombinant human FSH (FSH (invention); preparation 1: open squares, preparation 2: closed triangles) or FSH obtained from CHO cells (Gonal F; closed diamonds).
Figure 3:
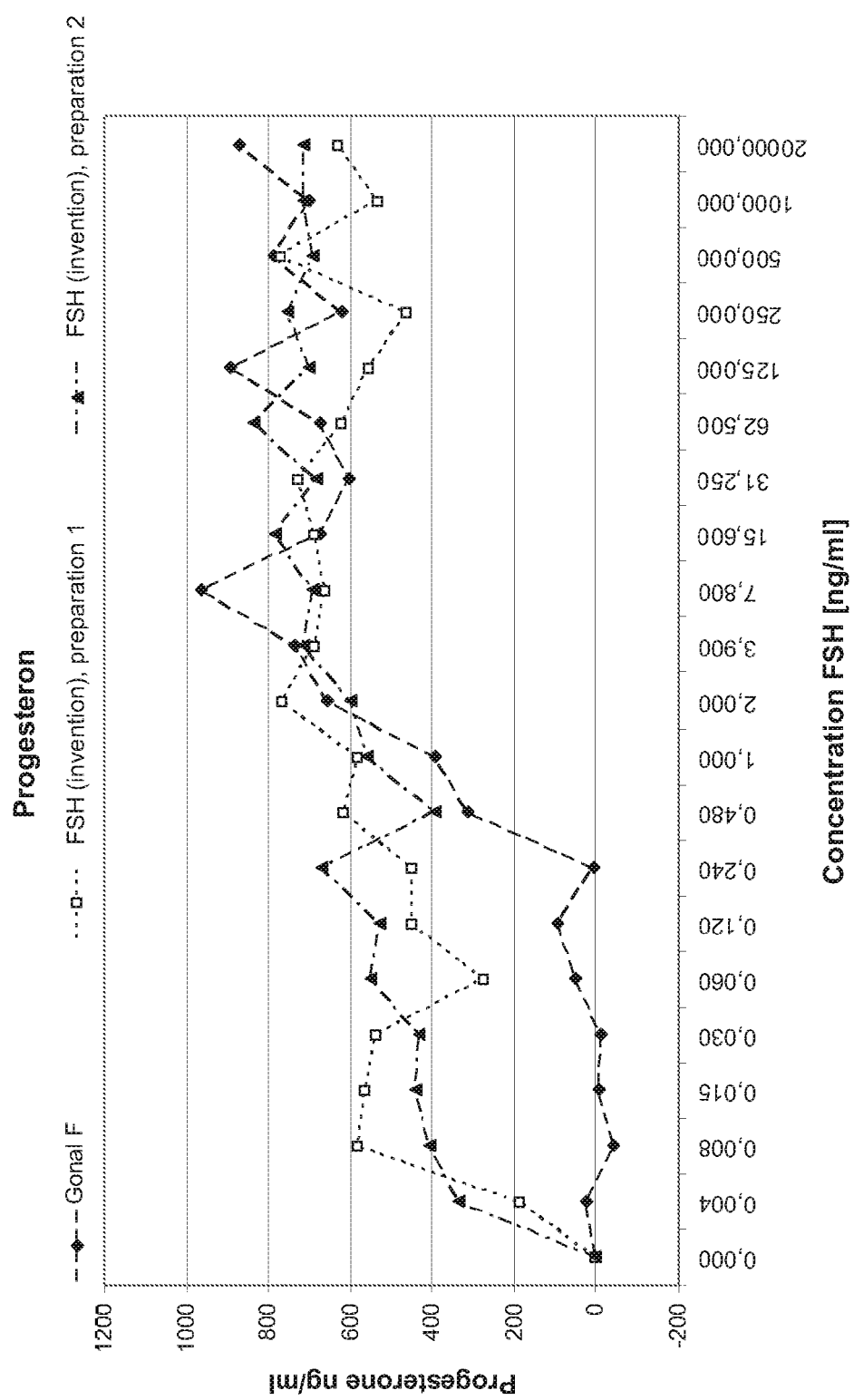
FIG. 3 shows the progesterone synthesis of isolated granulosa cells stimulated with different concentrations of the improved recombinant human FSH (FSH (invention); preparation 1: open squares, preparation 2: closed triangles) or FSH obtained from CHO cells (Gonal F; closed diamonds).
Figure 4:
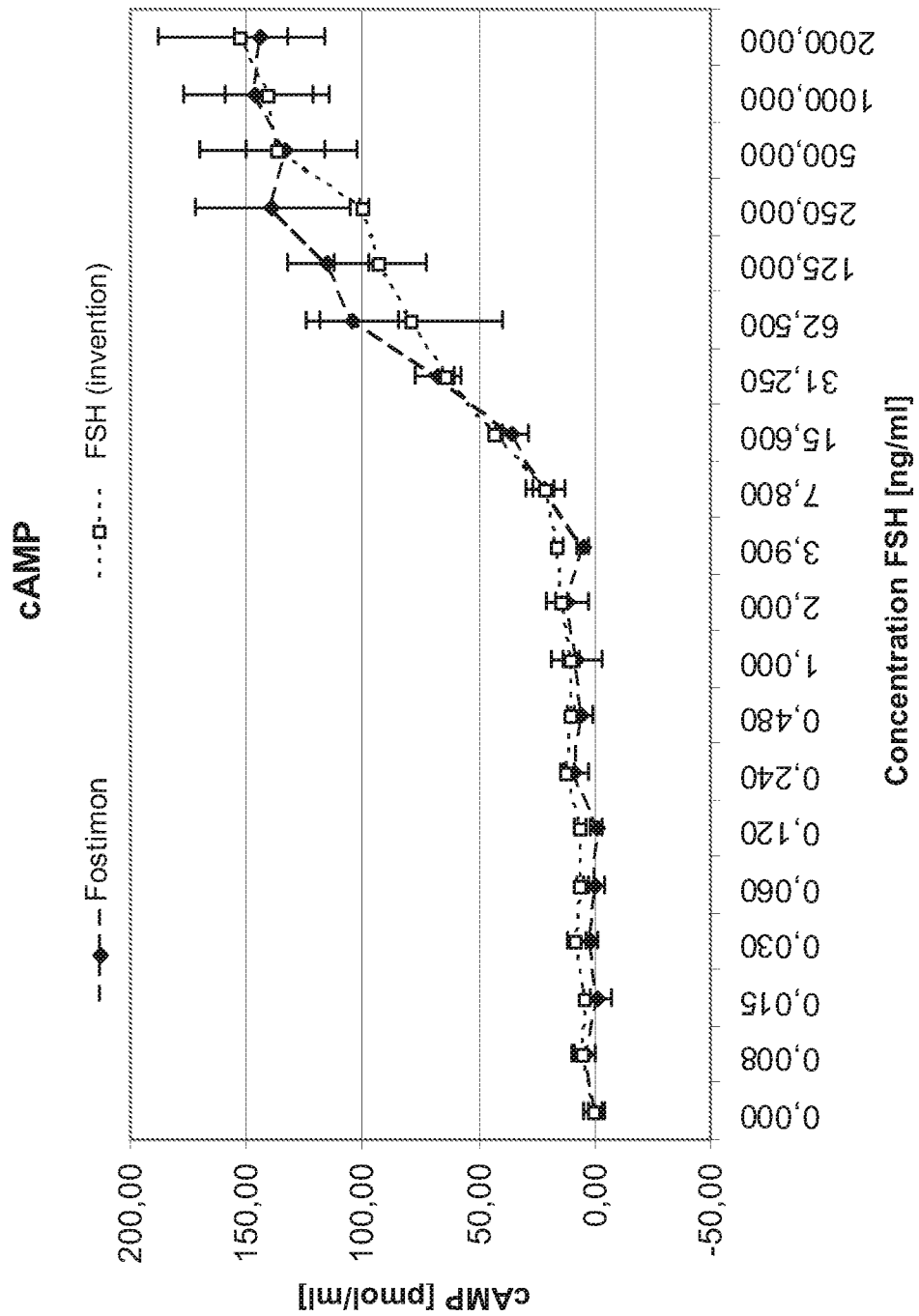
FIG. 4 shows the cAMP release of isolated granulosa cells stimulated with different concentrations of the improved recombinant human FSH (FSH (invention); open squares) or urinary FSH (Fostimon: closed diamonds).
Figure 5:
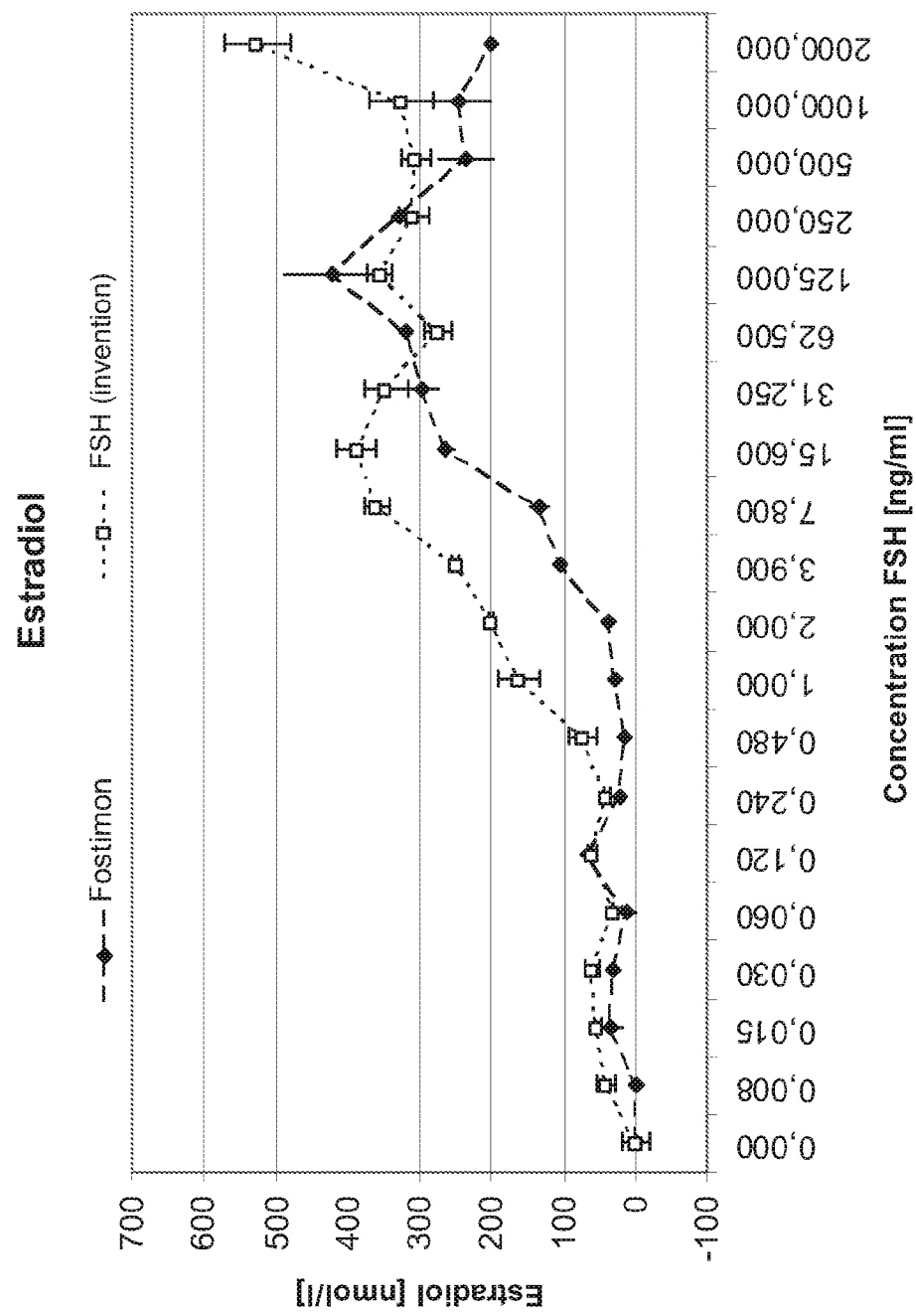
FIG. 5 shows the estradiol synthesis of isolated granulosa cells stimulated with different concentrations of the improved recombinant human FSH (FSH (invention); open squares) or urinary FSH (Fostimon; closed diamonds).
Figure 6:
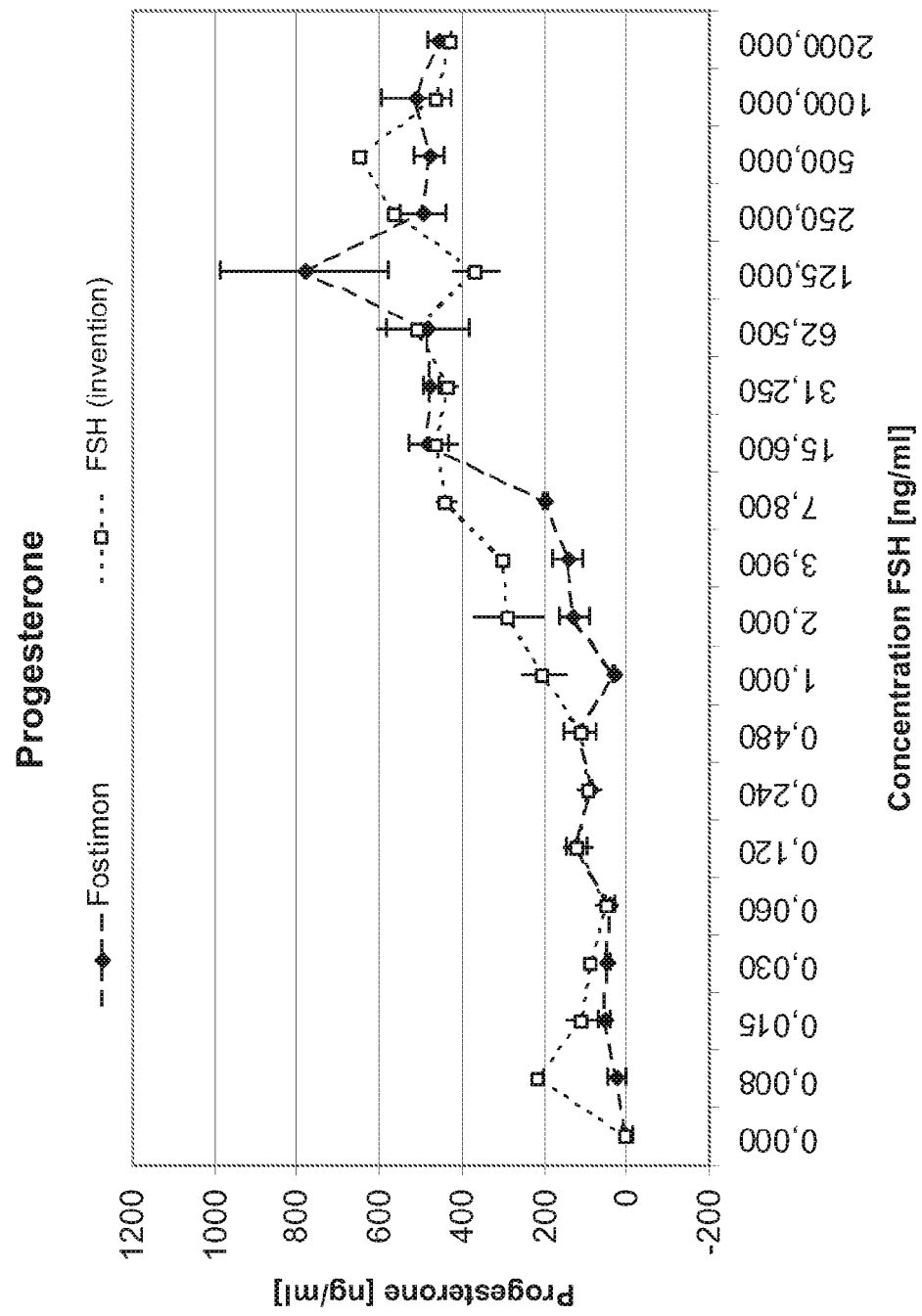
FIG. 6 shows the progesterone synthesis of isolated granulosa cells stimulated with different concentrations of the improved recombinant human FSH (FSH (invention); open squares) or urinary FSH (Fostimon; closed diamonds).

In order to perform a granulosa cell assay primary cells are isolated from the follicular fluid of IVF patients during the collection of the oocytes. After a Ficoll gradient centrifugation which eliminates other cell types as e.g. red blood cells the granulosa cells are seeded in 24 to 96 well plate format for 5-7 days in culture medium containing androstendione or testosterone. After that period, the cells (2 to $4*10^4$ cells per well) are stimulated with FSH ranging between 1 pg/ml to 2 μg/ml in the steps shown in the diagram (400 μl medium per well). After three to four hours incubation half of the supernatant is collected for performing the cAMP assay. Another 24 h later the cells are lysed by freeze thaw in the remaining supernatant. The lysate is applied in the progesterone and estradiol assays.
Comparison of FSH (Invention) and Gonal F In the first set of experiments FSH (invention) is compared to Gonal F (Merck Serono SA). Gonal F is FSH recombinantly produced in CHO cells. The results are shown in FIGS. 1 to 3. While the second messenger cAMP is produced at comparable FSH concentrations of Gonal F and FSH (invention) products in comparable amounts, the steroids progesterone and estradiol are released at much lower FSH concentrations in the case of FSH (invention) products compared to FSH recombinantly produced in CHO cells (Gonal F).
Comparison of FSH (Invention) and Fostimon In another set of experiments the FSH (invention) was compared against Fostimon (IBSA Institut Biochimigue SA), the FSH product isolated out of human urine. The results are shown in FIGS. 4 to 6. While the cAMP level rises similarly at comparable dose ranges of FSH for both products, the sex steroids are produced at a significantly lower concentration of FSH (invention) compared to Fostimon.

Note: Since the assays are performed using different donors, differences in the stimulation profile may account to the donors used in each assay.

Example 3

Steelman-Pohley Assay

Figure 7:
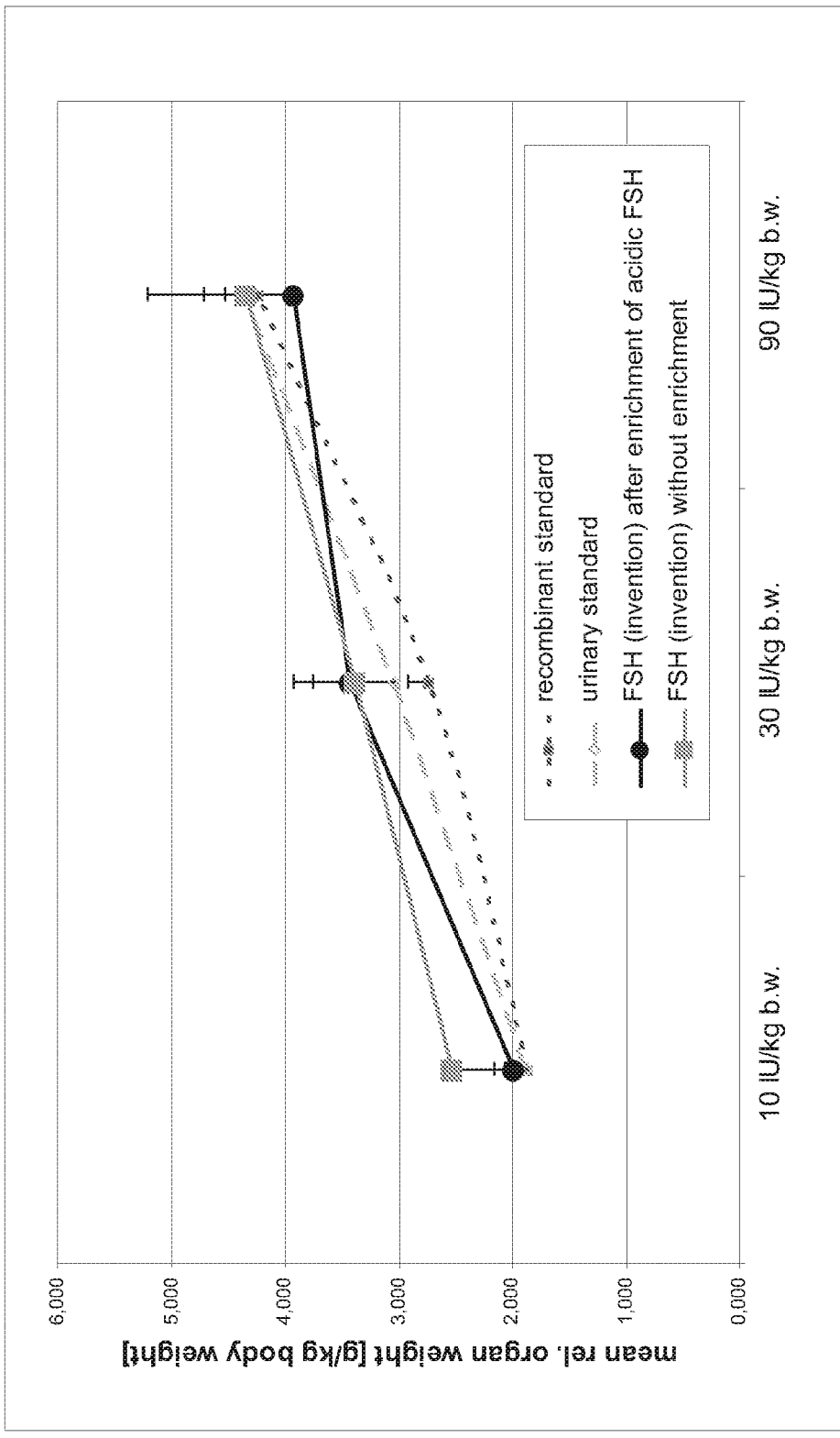
FIG. 7 shows the results of the Steelman-Pohley assay using the improved recombinant human FSH in comparison to standard urinary FSH and standard recombinant FSH obtained from CHO cells. The ovarian weight gain in immature female rats after daily administration for three days is plotted against the used FSH concentration.

The activity of FSH was also determined by the Steelman-Pohley assay. The assay was performed according to the pharmacopeia. In particular, the ovarian weight gain in immature female rats was measured after administration of three different FSH concentrations each given daily for three days. The potency is calculated using the parallel line evaluation. The results are shown in FIG. 7.

TABLE 2

Calculated activity of FSH (invention) after comparison with urinary FSH

| Sample | calculated activity |
|---|---|
| FSH (invention) without enrichment | 6,271 IU/mg |
| FSH (invention) with enrichment at pH 4.5 | 7,663 IU/mg |

Activity of the urinary standard: 7,135 IU/mg

As demonstrated by the Steelman-Pohley assay, the in vivo activities of the FSH (invention) and of the urinary and recombinant standard FSH are similar in rat.

Example 4

Glycoprofiling

The glycoprofiles of the different FSH preparations were determined by structural analysis of the glycosylation. Glycoprofiling generates information on the complex glycan structure of the glycosylation sites. For glycoprofiling the intact N-glycans are released from the protein core employing PNGase F. The digestion is performed in a gel or gel block for unambiguous workup. Free N-glycans are labeled with the fluorescence marker 2-aminobenzamide. The purified sample of N-glycans is separated by means of hydrophilic interaction chromatography (HILIC) with fluorometric detection. This analysis gave the following results:

TABLE 3

Relative amounts of the different glycosylation properties

| Sample | F | S | G | B |
|---|---|---|---|---|
| FSH (invention) | 80% | 90% | 98% | 42% |
| Fostimon | 48% | 83% | 91% | 28% |
| Puregon[1] | 29% | 91% | 91% | 0% |

F: fucose;
S: sialic acid;
G: galactose;
B: bisecting N-acetylgalactosamine
[1]literature values (Hård, K. et al. (1990) European Journal of Biochemistry 193, 263-271)
Shown are the relative amounts of N-glycans on the FSH which carry the indicated units. Puregon is another recombinant human FSH produced in CHO cells.

Furthermore, the ratio of 2,3-coupled and 2,6-coupled sialic acids in the glycans of the FSH was analyzed by comparing the amount of sialic acid released by sialidase A (cleaving off 2,3- and 2,6-coupled sialic acids) and sialidase S (cleaving off only 2,3-coupled sialic acids).

TABLE 4

Relative amounts of the sialic acid linkage

| Sample | 2,3-linked sialic acid | 2,6-linked sialic acid |
|---|---|---|
| FSH (invention) | 43% | 57% |
| Bravelle | 75% | 25% |
| Gonal F/ Puregon | 100% | 0% |

In FSH (invention), the sialic acid residues are coupled to the glycans by 2,3- as well as 2,6-bonds in a ratio of about 1:1, comprising even more 2,6-coupled sialic acids than 2,3-coupled sialic acids, while in the urinary FSH Bravelle (Ferring Pharmaceuticals Inc.) the ratio is about 3:1 in favor of 2,3-linked sialic acid. Due to their recombinant production in CHO cells, Puregon (Organon/EssexPharma) and Gonal F (Merck Serono) do not have any bisecting N-acetylgalactosamines and only comprises 2.3-coupled sialic acids.

Antennarity, terminal galactose units and Z-number were calculated from the above measurements and by determination of the charge distribution of the glycans after release from the FSH.

TABLE 5

Antennarity of the glycosylation of the different FSH

| Sample | Bi | Tri | Tetra |
|---|---|---|---|
| FSH (invention) | 42% | 35% | 22% |
| Fostimon | 39% | 45% | 16% |
| GonalF[1] | ~65% | ~25% | ~10% |
| Puregon[2] | 53% | 26% | 12% |

Bi: biantennary N-glycans; Tri: triantennary N-glycans; Tetra: tetraantennary N-glycans
[1]literature values (Gervais, A. et al. (2003) Glycobiology 13(3), 179-189)
[2]literature values (Hård, K. et al. (1990) European Journal of Biochemistry 193, 263-271)
Shown are the relative amounts of bi-, tri- and tetraantennary N-glycans on the FSH.

TABLE 6

Relative amount of terminal galactose units

| Sample | Terminal galactose |
|---|---|
| FSH (invention) | 75% |
| Fostimon | 43% |

Shown are the relative amounts of N-glycan branches on the FSH which have a galactose unit at their end.

TABLE 7

Z-number of different FSH

| Sample | Z-number |
|---|---|
| FSH (invention) without enrichment | 220 |
| FSH (invention) with enrichment of acidic isoforms | 245 |
| Gonal F (rFSH) | 218 |
| Puregon (rFSH) | 204 |
| Fostimon (uFSH) | 212 |
| Bravelle (uFSH) | 244 |

Shown is the Z-number, i.e. the relative acidity, of the FSH preparations. A higher Z-number indicates a more acidic FSH preparation.

In conclusion, the FSH according to the present invention (FSH (invention)) has a high degree of bisecting N-acetylglucosamine, a high antennarity and a high degree of sialylation, in particular after enrichment of the acidic isoforms, and a high sulfation degree. It is assumed that because of one or more of these three glycosylation parameters, the FSH (invention) has a superior activity compared to the common recombinant or urinary FSH preparations.

Furthermore, the FSH (invention) is also highly fucosylated and has a ratio of 2,3- to 2,6-sialylation of about 1:1 or even a higher amount of 2,6-sialylation.

Furthermore, the glycan structures of the FSH preparations were also analyzed by mass spectroscopy of the released glycans. The following results were obtained:

TABLE 8

Relative amounts of different glycosylation properties

| Sample | F | S0 | S1 | S2 | S3 | S4 | S > 0 | G0 | G1 | G2 | G3 | G4 | G > 0 | B |
|---|---|---|---|---|---|---|---|---|---|---|---|---|---|---|
| Gonal F | 55 | 1 | 16 | 45 | 28 | 9 | 98 | 0 | 1 | 55 | 30 | 14 | 100 | 0 |
| Bravelle | 43 | 1 | 11 | 45 | 34 | 9 | 99 | 0 | 7 | 39 | 39 | 14 | 99 | 14 |
| FSH (inv.) | 43 | 1 | 18 | 35 | 31 | 15 | 99 | 0 | 7 | 45 | 30 | 20 | 102 | 28 | shown are the relative amounts of glycans having the following property:
F: fucose; S0: no sialic acid; S1: one sialic acid; S2: two sialic acids; S3: three sialic acids; S4: four sialic acids; S > 0: at least one sialic acid; G0: no galactose; G1: one galactose; G2: two galactoses; G3: three galactoses; G4: four galactoses; G > 0: at least one galactose; B: bisecting GlcNAc

TABLE 9

Antennarity of the glycosylation of the different FSH

| Sample | Bi | Tri | Tetra |
|---|---|---|---|
| FSH (invention) | 48% | 31% | 21% |
| Bravelle | 45% | 43% | 12% |
| Gonal-f | 56% | 30% | 14% |

Bi: biantennary N-glycans;
Tri: triantennary N-glycans;
Tetra: tetraantennary N-glycans

TABLE 10

Relative amount of sulfated glycans

| Sample | Sulfation |
|---|---|
| FSH (invention) | 15% |
| Bravelle | 2% |
| Gonal F | 0 % |

Shown are the relative amounts of N-glycans on the FSH which carry a sulfate group.

Example 5

Pharmacological Effects

The pharmacological profile of FSH (invention) was investigated in different in vivo pharmacology and toxicology studies in female rats and monkeys and an in vivo bioassay. As molecular markers, estradiol and inhibin-B were used. These markers are released by the ovaries upon stimulation with FSH. Estradiol is responsible for follicle growth and maturation while inhibin-B is part of the natural negative feedback mechanism. Furthermore, inhibin-B was shown previously to be a good surrogate marker for the ovarian stimulation by FSH.

5.1 FSH treatment in Mature Rats

Upon treatment of mature female rats with single s.c. doses of 100 IU FSH (invention)/kg b.w., the serum inhibin-B levels increased 2-3 days following administration and decreased again to baseline levels. Repeated dosing of rats according to their oestrus cycle with 100 IU FSH (invention) resulted in a marked increase of serum progesterone and inhibin-B reflecting multiple ovulations followed by hormone production in luteal cells. Similar findings were observed in the dose range finding study where 7-d repeated doses of 1200 IU FSH (invention)/kg were administered. No difference of the pharmacodynamic activity of FSH (invention) compared to the FSH containing reference products (Gonal-f, Bravelle) investigated in the same studies could be observed.

In a 28-day repeated dose toxicity studies performed in female rats a dose-related enlargement of the ovaries and an increase in the number of Graafian follicles were observed for all dose groups (30, 100, 300 IU/kg b.w.). Correlating with these findings elevated inhibin-B levels compared to the control were noted during the treatment period. The inhibin-B levels of the treated animals were increased in a dose-related way starting at the low dose level of 30 IU FSH (invention)/kg b.w./day. All findings were completely reversible.

5.2 FSH Treatment in Mature Monkeys

Figure 8:
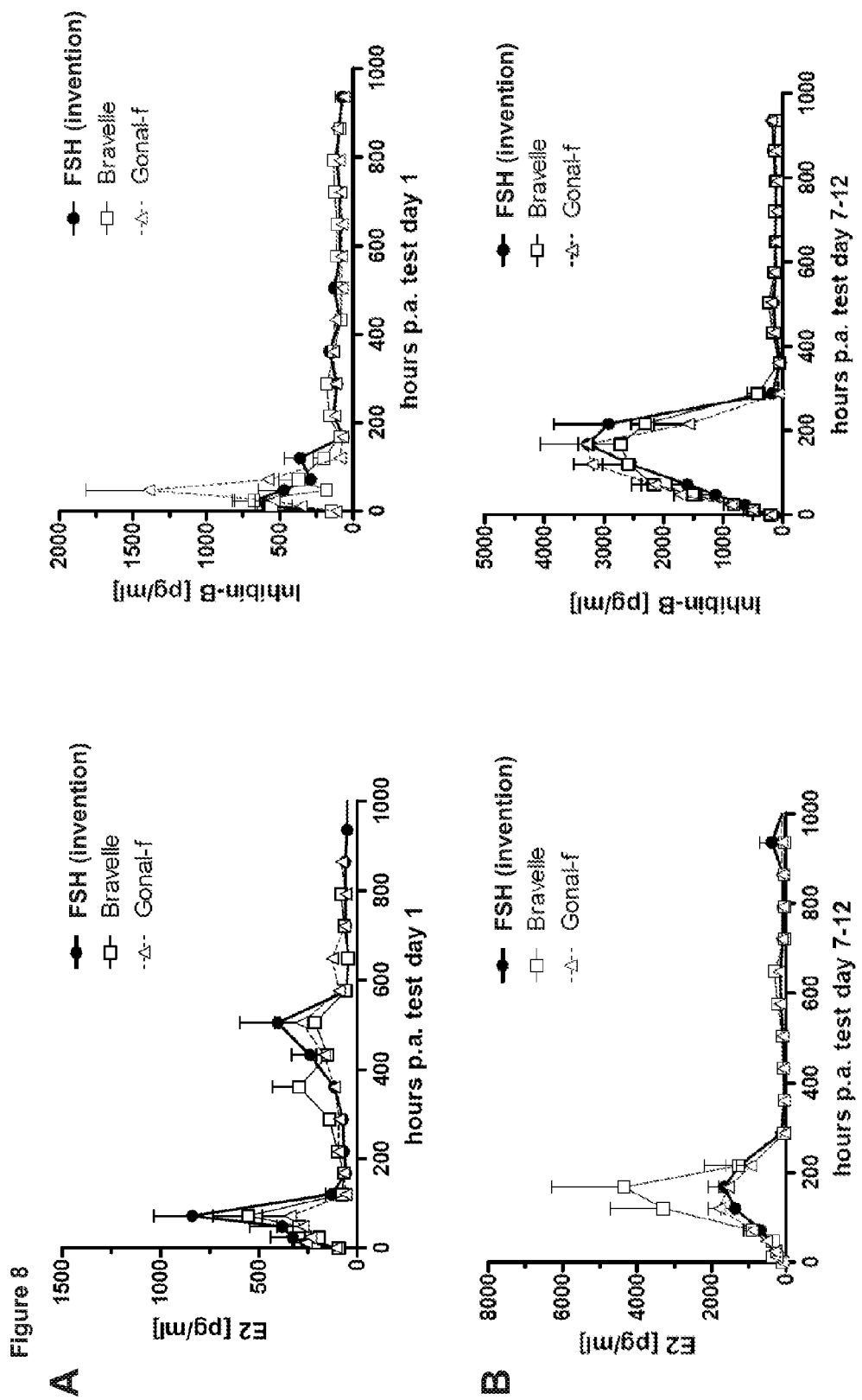
FIG. 8 shows serum concentrations of estradiol (E2) and inhibin-B observed in cynomolgus monkeys after single (A) and repeated (B) s.c. injection of FSH (invention), the urinary FSH Bravelle or the recombinant FSH Gonal-f expressed in CHO cells. Each bar represents mean and standard deviation of 4 animals.

The pharmacological profile after single and repeated doses of FSH (invention) was evaluated in cynomolgus monkeys. The cynomolgus monkey is considered the most relevant animal model based on the close similarities to human. The study consisted of a single dose administration of FSH to sexually mature, female animals exhibiting a regular menstrual cycle. The animals were randomly allocated to the test groups based on the phase of their oestrus cycle. The test item administration to the animals started 1 to 3 days after initiation of menses. The study included 4 groups, each comprising of 4 animals which were treated by a single s.c. bolus injection of 100 IU/kg b.w. of FSH (invention), the urinary FSH Bravelle or the recombinant FSH Gonal-f expressed in CHO cells. Blood sampling for the analysis of estradiol and inhibin-B levels was performed from all animals predose, and at the indicated time points after administration. The time points following administration were selected to reflect different phases of the oestrus cycle. The results are shown in FIG. 8A.

For all tested FSH substances, the estradiol and inhibin-B levels of the treated animals increased for 5 days following single administration of the test substances and decreased again to baseline levels. A normal mid-cycle estradiol surge was observed for nearly all animals at test days 14 to 22. FSH (invention) showed the highest increase in estradiol level. This experiment demonstrates at least a comparable pharmacological efficacy for FSH (invention) at lower AUC levels (see Example 6) indicating a higher activity in receptor stimulation.

Additionally, a similar study was performed wherein the monkeys received repeated FSH doses. The repeated dose study included 3 groups, each comprising of 4 animals which were treated by repeated daily s.c. bolus injections of 100 IU/kg b.w. FSH (invention), Bravelle or Gonal-f for 7 consecutive days. Blood sampling was as described for the single dose study. The estradiol and inhibin-B levels of the animals treated repeatedly s.c. with 100 IU FSH (invention)/kg b.w., 100 IU Bravelle/kg b.w. or 100 IU Gonal-f/kg b.w. increased over the whole treatment period of 7 days (see FIG. 8B). After the end of treatment the hormone levels decreased slowly and reached normal levels after 5-7 days. The maximum estradiol and inhibin-B concentrations observed after repeated administration of FSH (invention) were much higher compared to the concentrations observed after single dosing, and also compared to levels of the normal oestrus cycle. The pharmacodynamics effects observed after repeated s.c. administration of FSH (invention) were as expected for this product class and were comparable to the effects observed for the reference products in the same study.

Induction of Follicle Growth

A 4-week subchronic toxicity study with included analysis of pharmacodynamic parameters was performed in cynomolgus monkeys. 4 groups, each comprising of 4 female, sexually mature cynomolgus monkeys were treated with FSH (invention) by repeated subcutaneous injections once daily for 28 days. The dose levels were 30, 100, and 300 IU/kg b.w./day for low, intermediate, and high dose groups, respectively. Additionally to this main study, 2 female animals per group were scheduled for a 6-week recovery period for the control and for the high dose group. Blood samples for the analyses of estradiol and inhibin-B were withdrawn before and at the end of the treatment period (predose, day 1 and 28), 6 hours p.a. at day 17 and at the end of the recovery period (day 70).

Repeated treatment with 30, 100 or 300 IU FSH (invention)/kg b.w./day for 4 weeks resulted in increased absolute and relative ovary weights and in an increase in the number of Graafian follicles at terminal sacrifice. Additionally, a few animals of all dose groups revealed a slight decrease in the number of corpora lutea. Correlating to this finding, increased serum levels of estradiol and inhibin-B were observed in all dose groups.

5.3 Analysis of Adverse Effects

To analyze the risk of any unexpected adverse effects of FSH (invention), the major safety pharmacology parameters were included into a 4 week pivotal toxicity studies in rats and cynomolgus monkeys (ECG, heart rate, blood pressure, respiratory rate). These studies did not provide any evidence for a general action of FSH (invention) on the major systems, and thus, FSH (invention) can be considered as safe and does not show adverse side effects.

Example 6

Pharmacokinetics

The aim of the study was to investigate the bioavailability and pharmacology of FSH (invention) compared with Bravelle and Gonal-f by subcutaneous or intravenous administration to cynomolgus monkeys. The study was performed with sexually mature, female animals exhibiting a regular menstrual cycle. The animals were randomly allocated to the test groups based on the phase of their oestrus cycle. The test item administration to the animals started 1 to 3 days after initiation of menses. The study included 4 groups, each comprising 4 animals which were treated either by a single i.v. bolus injection of 100 IU/kg b.w. FSH (invention) or a single s.c. bolus injection of 100 IU/kg b.w. FSH (invention), Bravelle® or Gonal-f®. Blood sampling for the analysis of FSH levels was performed from all animals at different time points following administration reflecting different phases of the oestrus cycle.

None of the animals died prematurely during the course of the study or showed clinical signs of systemic toxicity. No test or reference item-related influence or local intolerance was noted.

Figure 9:
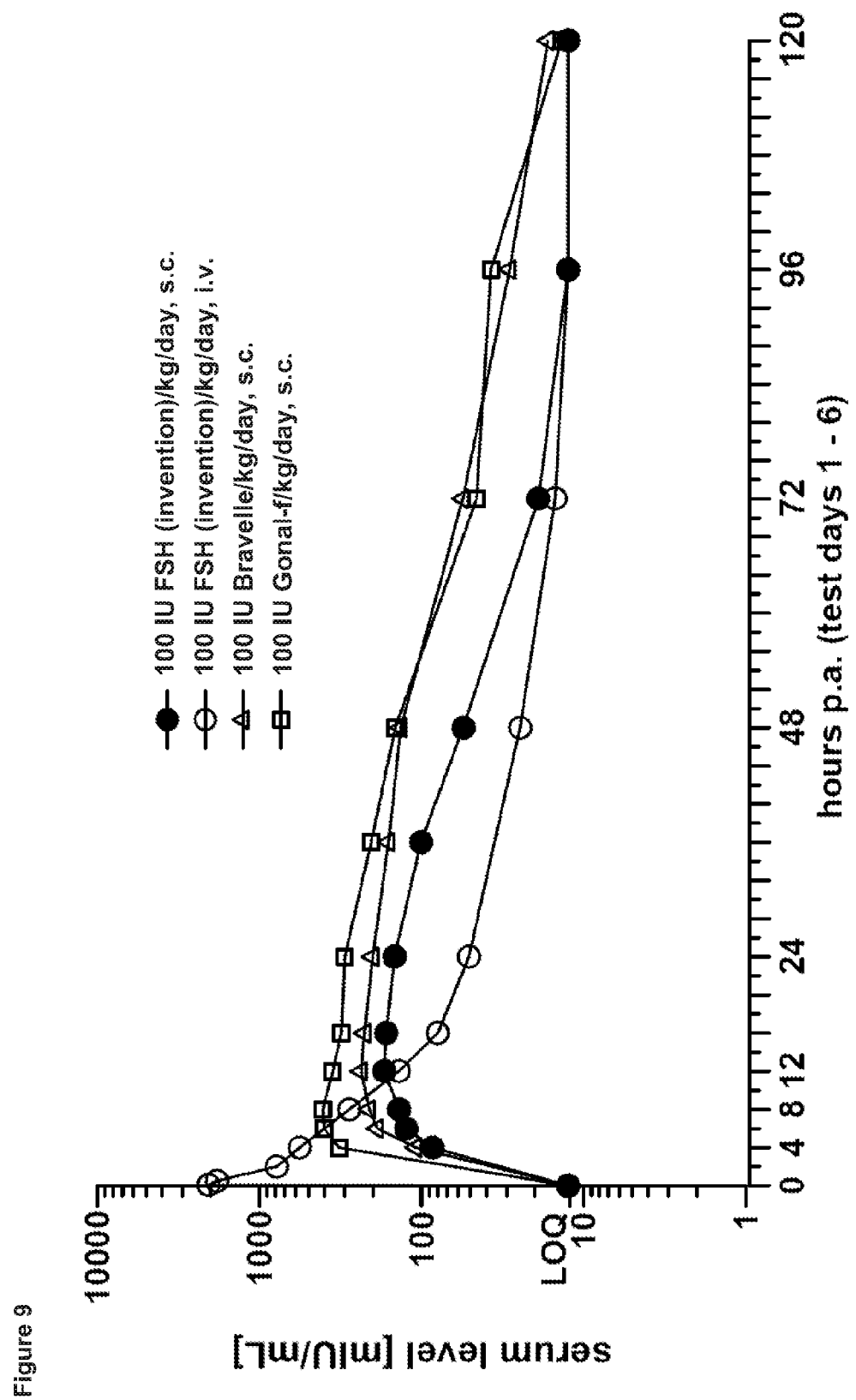
FIG. 9 shows serum concentrations of FSH in female cynomolgus monkeys after a single i.v. or s.c. injection. Each symbol represents the mean value of a group of 4 animals.

A $C_{max}$-level of 186.13 mIU FSH/mL was noted 8 hours p.a. after single s.c. treatment with 100 IU FSH (invention)/kg b.w. The calculated mean serum elimination half-life of FSH (invention) was 16.85 hours. Serum levels are presented in FIG. 9. The mean values of the toxicokinetic parameters in monkey serum following single exposure are given in Table 11.

and toxicological studies in monkeys which used doses of 10-1000 IU/kg b.w. Gonal-f. None of the animals died prematurely during the course of the study or showed clinical signs of systemic toxicity. No test or reference item-related influence or local intolerance was noted. The results showed that Cmax- and AUC-values of FSH (invention) in monkeys compared to the FSH containing reference products (Gonal-f, Bravelle) are reduced, resulting in a lower drug exposure in FSH (invention) treated animals. Nevertheless, pharmacology data obtained in the same studies have shown that there is no difference between the FSH products in respect to their ability to stimulate estradiol and inhibin-B production as effectors of the FSH receptor (see Example 5).

Nude female mice were administered 5 μg FSH by s.c. injection and the FSH concentration in blood was monitored. The pharmacokinetic profiles FSH (invention) as well as Gonal-f and Bravelle are largely comparable in respect to Cmax and $AUC_{0-t\ last}$-values. Cmax levels of 5.1±1.9% ID, 6.7±0.4% ID and 5.5±0.4% ID were observed after single subcutaneous injection of FSH (invention), Bravelle and Gonal-f, respectively. $AUC_{0-t\ last}$-values of 71.6±25.4% ID, 99.1±12.9% ID and 79.7±9.7% ID were observed for FSH (invention). Bravelle and Gonal-f. respectively. Generally the clearance from the blood and the relative drug exposure is comparable for all substances investigated; no statistically relevant differences were measured. Upon investigation of the biodistribution of the administered FSH, an accumulation of FSH in the ovaries and uterus was observed (besides a high accumulation in the kidneys due to their role in elimination of the FSH from the body).

TABLE 11

Toxicokinetic parameters calculated after a single s.c. bolus injection of FSH to female cynomolgus monkeys.
NON-COMPARTMENTAL ANALYSIS OF FSH FOLLOWING SINGLE EXPOSURE

| $C_{MAX}$# [MIU/ML] | $T_{MAX}$# [H] | $T_{1/2}$ [H] | $K_{EL}$ [1/H] | $AUC_{0-T\ LAST}$ [MIU/ML*H] | $AUC_{0-\infty}$ [MIU/ML*H] | CI [ML/MIN/KG] | F FOR FSH (INV) [%] | RELATIVE EXPOSURE## (GR. 1 = 1.0) |
|---|---|---|---|---|---|---|---|---|
| TEST DAYS 1-2 | | | | | | | | |
| GROUP 1:100 IU FSH (INVENTION)/KG B.W., S.C. | | | | | | | | |
| 186.13 | 14.00 | 16.65 | 0.041 | 6363.50 | 7017.07 | 0.243 | 72.77 | 1.0 |
| GROUP 2: 100 IU FSH (INVENTION)/KG B.W., I.V. | | | | | | | | |
| 2161.33 | 0.29 | 6.66 | 0.064 | 6744.45 | 11068.16 | 0.163 | — | 1.37 |
| GROUP 3: 100 IU BRAVELLE ®/KG B.W., S.C. | | | | | | | | |
| 241.73 | 15.00 | 20.97 | 0.035 | 11931.93 | 12532.51 | 0.145 | n.a. | 1.88 |
| GROUP 4: 100 IU GONAL-F ®/KG B.W., S.C. | | | | | | | | |
| 456.48 | 12.00 | 18.33 | 0.038 | 16109.68 | 16671.93 | 0.102 | n.a. | 2.53 |

Values obtained from serum analysis of FSH
n.a.: Not applicable
F: Relative bioavailability for FSH (invention)
[(AUC$_{0-t\ last}$ s.c. × dose i.v.)/(AUC$_{0-t\ last}$ i.v. × dose s.c.)] × 100%
Comparison of the AUC$_{0-t\ last}$ values, group 1 = 1.00
A relative bioavailability (F) of 72.77% was calculated for FSH (invention) following subcutaneous administration compared to FSH (invention) administered intravenously. The following FSH-exposure ratios were noted following single exposure: FSH (invention) (s.c.) < FSH (invention) (i.v.) < Bravelle < Gonal-f.

Similar data was also obtained from multiple dose studies in cynomolgus monkeys and from studies in rats and nude mice:

The repeated dose study in cynomolgus monkeys was performed similar to the single dose study. The study included 3 groups, each comprising of 4 animals which were treated by repeated daily s.c. bolus injections of 100 IU/kg b.w. FSH (invention), Bravelle or Gonal-f for 7 consecutive days. The dose was selected referring to pharmacokinetic Mature female rats were given single or multiple doses of 100 IU/kg b.w. FSH (invention), Bravelle or Gonal-f by s.c. injection and the serum concentration of FSH was monitored. The results showed that serum half-live and AUC-values of FSH (invention) in rats compared to the FSH containing reference products (Gonal-f, Bravelle) are reduced, resulting in a lower drug exposure in FSH (invention) treated animals. Nevertheless, pharmacology data obtained in the same studies have shown that there is no difference between the FSH products in respect to their ability to stimulate estradiol and inhibin-B production as effectors of the FSH receptor (see Example 5).

Example 7

Pharmacokinetics and Pharmacodynamics in Humans

In a clinical study, FSH (invention) was administered to volunteers and the pharmacokinetic and pharmacodynamic parameters were determined. Healthy female volunteers received 25 IU, 75 IU or 150 IU FSH (invention) in a single s.c. dose and the FSH concentration in the circulation was monitored. Additionally, also the number and size of the follicles were analyzed prior to and after the medication.

As a preliminary result, almost a doubling of the maximum serum concentration of FSH (invention) (Cmax) compared to published data of urinary and recombinant FSH measured by different labs was observed. The circulation half-life ($t_{1/2}$) after subcutaneous administration is comparable for FSH (invention) (~33 h±3 h), recombinant CHO-cell derived FSH (Gonal-f: 37 h±28 h (le Cotonnec et al. (1994) Fertility and Sterility 61, 679-686) and urinary FSH (MetrodinHP: 45 h±21 h (le Cotonnec et al. (1993) Human Reproduction 8, 1604-1611). The pharmacodynamic data showed that follicle growth can be seen for some patients already with a single dose of 25 IU FSH (invention). This could not be observed in the case of the comparators Bravelle and Gonal-f. In the case of 75 and 150 IU FSH (invention) all subjects showed enlarged follicles with one patient having one follicle doubled in size.

The invention claimed is:

1. A recombinant follicle-stimulating hormone (FSH) preparation, wherein the recombinant FSH in the preparation has a glycosylation pattern comprising the following characteristics:
   (i) a relative amount of glycans carrying bisecting N-acetylglucosamine (bisGlcNAc) of at least 20% of the total amount of glycans attached to FSH in the preparation,
   (ii) a relative amount of 2,6-coupled sialic acid of at least 30% of the total amount of sialic acids,
   (iii) a Z number of at least 200; and
   (iv) at least 17% of the glycan structures are tetraantennary.

2. The recombinant follicle-stimulating hormone (FSH) preparation according to claim 1, obtainable by production in the human cell line GT 5s.

3. The recombinant FSH preparation according to claim 1, which comprises one or more of the following characteristics
   (a) the glycosylation pattern comprises a relative amount of glycans carrying one or more sialic acid residues of at least 85%;
   (b) the glycosylation pattern comprises a relative amount of tetraantennary glycans of at least 18%;
   (c) a Z-number of at least 200;
   (d) it is human recombinant FSH;
   (e) it is produced by a human cell line or human cells; and/or
   (f) the FSH in the preparation comprises an alpha subunit having the amino acid sequence of SEQ ID NO: 1 and a beta subunit having the amino acid sequence of SEQ ID NO: 2.

4. The recombinant FSH preparation according to claim 1, wherein the glycosylation pattern comprises one or more of the following characteristics:
   (i) a relative amount of glycans carrying bisecting N-acetylglucosamine (bisGlcNAc) in the range of from about 25% to about 50%;
   (ii) a relative amount of tetraantennary glycans of at least 16%;
   (iii) a relative amount of glycans carrying fucose of at least 35%;
   (iv) a relative amount of 2,6-coupled sialic acid of at least 53%;
   (v) a relative amount of glycans carrying one or more sialic acid residues of at least 88%;
   (vi) a Z-number of at least 220;
   (vii) a relative amount of glycans carrying galactose of at least 95%;
      (viii) a relative amount of glycan branches carrying a terminal galactose unit optionally modified by a sialic acid residue of at least 60%;
   (ix) a relative amount of glycans carrying a sulfate group of at least 3%;
   (x) it comprises at least 45 different glycan structures, wherein each one of the different glycan structures has a relative amount of at least 0.05% of the total amount of glycan structures of the FSH in the preparation;
   (xi) it comprises at least 35 different glycan structures, wherein each one of the different glycan structures has a relative amount of at least 0.1% of the total amount of glycan structures of the FSH in the preparation;
   (xiii) it comprises at least 20 different glycan structures, wherein each one of the different glycan structures has a relative amount of at least 0.5% of the total amount of glycan structures of the FSH in the preparation; and/or
   (xiv) it comprises at least 40% more different glycan structures than FSH obtained from CHO cells in a corresponding preparation, wherein each one of the different glycan structures has a relative amount of at least 0.05% of the total amount of glycan structures of the FSH in the respective preparation.

5. The recombinant FSH preparation according to claim 1, wherein the glycosylation pattern comprises the following characteristics:
   (i) a relative amount of glycans carrying bisecting N-acetylglucosamine (bisGlcNAc) in the range of from about 5% to about 50%;
   (ii) a relative amount of tetraantennary glycans of at least 17%;
   (iii) a relative amount of glycans carrying fucose of at least 35%;
   (iv) a relative amount of 2,6-coupled sialic acid in the range of from about 53% to about 99%; and
   (v) a relative amount of glycans carrying one or more sialic acid residues of at least 88%.

6. The recombinant FSH preparation according to claim 1, wherein the recombinant FSH in the preparation has a glycosylation pattern according to any one of the following embodiments:

| Embodiment | B | 2,6-S | sulfate | S > 0 | Z | tetra |
| --- | --- | --- | --- | --- | --- | --- |
| 1 | ≥20 | ≥53 | ≥2.5 | | | |
| 2 | ≥20 | ≥53 | ≥2.5 | ≥80 | ≥200 | ≥17 |
| 3 | ≥20 | ≥53 | ≥2.5 | ≥85 | | |
| 4 | ≥20 | ≥53 | ≥2.5 | | ≥220 | |
| 5 | ≥20 | ≥53 | ≥2.5 | | | ≥17 |
| 6 | ≥20 | ≥53 | ≥2.5 | ≥85 | ≥220 | ≥17 |
| 7 | 20-50 | ≥53 | ≥2.5 | | | |
| 8 | ≥20 | 53-80 | ≥2.5 | | | |
| 9 | ≥20 | ≥53 | 2.5-30 | | | |
| 10 | ≥20 | ≥53 | ≥2.5 | ≥80 | 200-260 | ≥17 |
| 11 | ≥20 | ≥53 | ≥2.5 | ≥80 | ≥200 | 17-30 |
| 12 | 20-50 | 53-80 | 2.5-30 | 80-100 | 200-260 | 17-30 |
| 13 | ≥25 | ≥55 | ≥3 | | | |
| 14 | ≥30 | ≥55 | ≥3 | | | |
| 15 | ≥25 | ≥60 | ≥3 | | | |
| 16 | ≥25 | ≥55 | ≥10 | | | |
| 17 | ≥30 | ≥60 | ≥10 | | | |
| 18 | ≥25 | ≥55 | ≥3 | ≥80 | ≥200 | ≥17 |
| 19 | ≥25 | ≥55 | ≥3 | ≥85 | ≥220 | ≥17 |
| 20 | ≥30 | ≥60 | ≥10 | ≥85 | ≥220 | ≥17 | wherein:
   (a) "B" is the percent of bisecting GlcNAc,
   (b) "2,6-S" is the percent of 2,6-coupled sialic acids,
   (c) "sulfate" is the percent of sulfated glycans,
   (d) "S>0" is the percent of sialic acids,
   (e) "tetra" is the number of tetraantennary glycans; and
   (f) "Z" is the Z number, wherein the Z number is calculated with the equation $Z = A1\% * 1 + A2\% * 2 + A3\% * 3 + A4\% * 4$, and wherein:
      (i) A1% is the percentage of glycans with a charge of −1,
      (ii) A2% is the percentage of glycans with a charge of −2,
      (iii) A3% is the percentage of glycans with a charge of −3; and
      (iv) A4% is the percentage of glycans with a charge of −4.

7. The recombinant FSH preparation according to claim 1, wherein said FSH is capable of stimulating the release of progesterone in granulosa cells
   (a) at concentrations where no significant amounts of cAMP are released; and/or
   (b) by inducing a signal transduction pathway which is independent of cAMP signaling.

8. The recombinant FSH preparation according to claim 1, wherein said FSH is capable of stimulating or co-stimulating germ cell maturation by a biological process which is independent of cAMP signaling.

9. The recombinant FSH preparation according to claim 1, wherein the FSH has one or more of the following characteristics as can be determined in a granulosa cell assay
   (a) it is capable of stimulating the release of progesterone in granulosa cells at concentrations which are below the minimum concentration needed for the induction of cAMP release by the granulosa cells;
   (b) it is capable of stimulating the release of at least 200 ng/ml progesterone in about $5*10^4$ to about $1*10^5$ granulosa cells/ml at FSH concentrations which do not induce a cAMP release or which induce a cAMP release of less than 10 pmol/ml;
   (c) it is capable of stimulating the release of at least 100 ng/ml progesterone in about $5*10^4$ to about $1*10^5$ granulosa cells/ml at a concentration that is lower than the concentration needed by human urinary FSH or recombinant FSH produced in CHO cells (Gonal F); and/or
   (d) it is capable of stimulating the release of at least 100 ng/ml progesterone in about $5*10^4$ to about $1*10^5$ granulosa cells/ml at a concentration wherein human urinary FSH or recombinant FSH produced in CHO cells (Gonal F) do not result in a corresponding release of progesterone.

10. The recombinant FSH preparation according to claim 1, wherein the FSH is capable of inducing follicle growth in a female human being after administration of a single dose, wherein the single dose preferably comprises 25 to 500 IU FSH and preferably is administered parenteral, in particular by subcutaneous injection.

11. A pharmaceutical composition comprising the recombinant FSH preparation according to claim 1.

12. The pharmaceutical composition according to claim 11, being in the form of a single unit dose comprising about 50 IU to about 400 IU FSH.

13. The recombinant FSH preparation according to claim 10, wherein the single dose comprises 25 to 500 IU FSH and is administered parenterally by subcutaneous injection.

14. The recombinant FSH preparation according to claim 1, wherein the glycosylation pattern further comprises a relative amount of glycans carrying fucose of at least 30% of the total amount of glycans attached to FSH in the preparation.

15. The recombinant FSH preparation according to claim 1, wherein the glycosylation pattern is a diverse glycosylation pattern.

16. The recombinant FSH preparation according to claim 1, wherein the recombinant FSH in the preparation has a glycosylation pattern comprising the following characteristics:
   (i) a relative amount of glycans carrying bisecting N-acetylglucosamine (bisGlcNAc) of at least 25% of the total amount of glycans attached to FSH in the preparation; and
   (ii) a relative amount of 2,6-coupled sialic acid of at least 40% of the total amount of sialic acids.

17. The recombinant FSH preparation according to claim 16, wherein the recombinant FSH in the preparation has a glycosylation pattern comprising the following characteristics:
   (i) a relative amount of glycans carrying bisecting N-acetylglucosamine (bisGlcNAc) of at least 30% of the total amount of glycans attached to FSH in the preparation; and
   (ii) a relative amount of 2,6-coupled sialic acid of at least 50% of the total amount of sialic acids.

* * * * *

UNITED STATES PATENT AND TRADEMARK OFFICE
CERTIFICATE OF CORRECTION

PATENT NO. : 9,527,899 B2
APPLICATION NO. : 13/814059
DATED : December 27, 2016
INVENTOR(S) : Steffen Goletz et al.

It is certified that error appears in the above-identified patent and that said Letters Patent is hereby corrected as shown below:

In the Claims

In Column 31, Line 17, in Claim 2, delete "GT 5s." and insert -- GT-5s. --, therefor.

In Column 31, Line 41, in Claim 4, delete "16%" and insert -- 17% --, therefor.

In Column 32, Line 15, in Claim 5, delete "about 5% to about 50%;" and insert -- about 25% to about 50%; --, therefor.

Signed and Sealed this
Nineteenth Day of June, 2018

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 9,527,899 B2 | Page 1 of 1 |
| APPLICATION NO. | : 13/814059 | |
| DATED | : December 27, 2016 | |
| INVENTOR(S) | : Steffen Goletz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this
Sixth Day of December, 2022

Katherine Kelly Vidal
*Director of the United States Patent and Trademark Office*